United States Patent
Oishi

(10) Patent No.: US 9,328,401 B2
(45) Date of Patent: May 3, 2016

(54) COPPER ALLOY CASTING HAVING EXCELLENT MACHINABILITY, STRENGTH, WEAR RESISTANCE AND CORROSION RESISTANCE AND METHOD OF CASTING THE SAME

(75) Inventor: Keiichiro Oishi, Yao (JP)

(73) Assignee: MITSUBISHI SHINDOH CO., LTD., Tokyo (JP)

( * ) Notice: Subject to any disclaimer, the term of this patent is extended or adjusted under 35 U.S.C. 154(b) by 861 days.

(21) Appl. No.: 11/573,632

(22) PCT Filed: Aug. 10, 2005

(86) PCT No.: PCT/JP2005/014697
§ 371 (c)(1),
(2), (4) Date: Feb. 12, 2007

(87) PCT Pub. No.: WO2006/016629
PCT Pub. Date: Feb. 16, 2006

(65) Prior Publication Data
US 2009/0014097 A1    Jan. 15, 2009

(30) Foreign Application Priority Data
Aug. 10, 2004  (JP) .................................. 2004-233952

(51) Int. Cl.
| | |
|---|---|
| *C22C 9/04* | (2006.01) |
| *C22C 9/02* | (2006.01) |
| *B22D 21/02* | (2006.01) |
| *C22C 1/06* | (2006.01) |
| *C22C 30/02* | (2006.01) |
| *C22C 30/06* | (2006.01) |

(Continued)

(52) U.S. Cl.
CPC .............. *C22C 9/04* (2013.01); *B22D 21/022* (2013.01); *B22D 21/025* (2013.01); *B22D 27/00* (2013.01); *C22C 1/03* (2013.01); *C22C 1/06* (2013.01); *C22C 9/00* (2013.01); *C22C 30/02* (2013.01); *C22C 30/06* (2013.01); *C22F 1/08* (2013.01)

(58) Field of Classification Search
None
See application file for complete search history.

(56) References Cited

U.S. PATENT DOCUMENTS

| | | | |
|---|---|---|---|
| 2,521,663 | A | 9/1950 | Zunick |
| 3,676,083 | A | 7/1972 | Cheney et al. |

(Continued)

FOREIGN PATENT DOCUMENTS

| | | | | |
|---|---|---|---|---|
| EP | 1681360 | * | 7/2006 | ................ C22C 9/00 |
| JP | 38-20467 | | 10/1938 | |

(Continued)

OTHER PUBLICATIONS

English translation of JP 2000-119775.*

(Continued)

*Primary Examiner* — Yoshitoshi Takeuchi
(74) *Attorney, Agent, or Firm* — Griffin and Szipl PC

(57) ABSTRACT

A copper alloy casting with excellent machinability, strength, wear resistance and corrosion resistance contains Sn: 0.5 to 15 mass %; Zr: 0.001 to 0.049 mass %; P: 0.01 to 0.35 mass %; one or more elements selected from Pb: 0.01 to 15 mass %, Bi: 0.01 to 15 mass %, Se: 0.01 to 1.2 mass %, and Te: 0.05 to 1.2 mass %; and Cu: 73 mass % or more serving as a remainder. In this case, f1=[P]/[Zr]=0.5 to 100, f2=3[Sn]/[Zr]=300 to 15000, and f3=3[Sn]/[P]=40 to 2500 (the content of an element 'a' is expressed as [a] mass %). The total content of α, γ and δ-phases is 95% or more, and the mean grain size is 300 μm or less.

18 Claims, 6 Drawing Sheets

(51) Int. Cl.
*C22F 1/08* (2006.01)
*B22D 27/00* (2006.01)
*C22C 1/03* (2006.01)
*C22C 9/00* (2006.01)

(56) References Cited

U.S. PATENT DOCUMENTS

| | | | |
|---|---|---|---|
| 3,912,552 A | | 10/1975 | Schultz et al. |
| 3,928,028 A | | 12/1975 | Yarwood |
| 4,047,978 A | | 9/1977 | Parikh et al. |
| 4,110,132 A | | 8/1978 | Parikh et al. |
| 4,238,249 A | | 12/1980 | Ruchel |
| 4,353,415 A | | 10/1982 | Klaschka et al. |
| 4,708,739 A | * | 11/1987 | Kellie et al. ............. 75/304 |
| 4,710,349 A | | 12/1987 | Yamazaki et al. |
| 4,786,469 A | * | 11/1988 | Weber et al. ........... 420/469 |
| 4,822,560 A | | 4/1989 | Oyama et al. |
| 4,826,736 A | | 5/1989 | Nakamura et al. |
| 5,370,840 A | | 12/1994 | Caron et al. |
| 5,565,045 A | | 10/1996 | Caron et al. |
| 5,871,861 A | | 2/1999 | Hirokou et al. |
| 6,401,323 B1 | | 6/2002 | Roller et al. |
| 6,413,330 B1 | | 7/2002 | Oishi |
| 6,627,011 B2 | | 9/2003 | Sugawara et al. |
| 2002/0006351 A1 | | 1/2002 | Sugawara et al. |
| 2004/0234412 A1 | * | 11/2004 | Oishi et al. ............. 420/477 |
| 2005/0039827 A1 | | 2/2005 | Yamagishi et al. |
| 2006/0222557 A1 | | 10/2006 | Pike, Jr. |
| 2008/0073005 A1 | | 3/2008 | Buck |
| 2010/0297464 A1 | | 11/2010 | Oishi |

FOREIGN PATENT DOCUMENTS

| | | | | |
|---|---|---|---|---|
| JP | 49-40226 | | 4/1974 | |
| JP | 50-078519 | | 6/1975 | |
| JP | 52-107227 | | 9/1977 | |
| JP | 54-92516 | | 7/1979 | |
| JP | 55-070494 | | 5/1980 | |
| JP | 58-39900 | | 9/1983 | |
| JP | 61-000542 | | 1/1986 | |
| JP | 61-48547 A | | 3/1986 | |
| JP | 61-133357 A | | 6/1986 | |
| JP | 62-274036 | | 11/1987 | |
| JP | 62-297429 | | 12/1987 | |
| JP | 1-162737 | | 6/1989 | |
| JP | 02-170954 A | | 7/1990 | |
| JP | 3-291344 | | 12/1991 | |
| JP | 04-224645 A | | 8/1992 | |
| JP | 6-058688 | | 3/1994 | |
| JP | 6-184669 | | 7/1994 | |
| JP | 6-184674 | * | 7/1994 | ............. C22C 9/02 |
| JP | 10-46270 A | | 2/1998 | |
| JP | 10-152735 A | | 6/1998 | |
| JP | 11-001736 | * | 1/1999 | ............. C22C 9/04 |
| JP | H 11-58034 | * | 3/1999 | ............. B22D 19/00 |
| JP | 2000-119775 | * | 4/2000 | ............. C22C 9/04 |
| JP | 2000-199023 | | 7/2000 | |
| JP | 2001-247923 | | 9/2001 | |
| JP | 2002-030364 A | | 1/2002 | |
| JP | WO2004/022805 | * | 3/2004 | ............. C22C 9/04 |
| JP | 2004-100041 | | 4/2004 | |
| JP | 2004-100042 | | 4/2004 | |
| JP | 2004-143541 | | 5/2004 | |
| JP | 2004-183056 A1 | | 7/2004 | |
| JP | 2004233952 A | | 8/2004 | |
| WO | 94/10352 | | 5/1994 | |

OTHER PUBLICATIONS

English translation for JP 6-184674 (1994).*
English translation of JPH 11-58034 (1999).*
English translation of JP 11-001736 (1999).*
Restriction/Election issued in co-pending U.S. Appl. No. 11/573,640, mailed Sep. 25, 2009.
The Metals Handbook Ninth Edition, Metallography and Microstructures, (American Society for Metals), Metals Park, Ohio, vol. 9, pp. 629-631 (Exhibit A).
The NDT Resource Center webpage (www.ndt-ed.org/Education Resources/CommunityCollege/PenetrantTest/Introduction/visualacuity.htm, (Exhibit B).
Office Action issued in co-pending related U.S. Appl. No. 11/573,638, mailed Jul. 6, 2010.
"Exhibit A" (Metals Handbook Ninth Edition, vol. 9, Metallography and Microstructures, American Society for Metals, pp. 641-642).
"Exhibit B" (Metals Handbook 8th Edition, vol. 7, Atlas of Microstructures of Industrial Alloys, American Society for Metals, pp. 290 & B-2).
"Exhibit C" (Metal Handbook Ninth Edition, vol. 9 Metallography and Microstructures, American Society for Metals, pp. 629-631).
Exhibit D (Binary Alloy Phase Diagrams, vol. 1, American Society for Metals, pp. 819-820, 971, 982 and 19).
p. 286 of Metals Handbook 8th Edition, vol. 7, Atlas of Microstructures of Industrial Alloys, 1972.
Cast Nonferous: Heat Treating of Copper and Copper Alloys, downloaded Nov. 2, 2010, from http://www.keytometals.com/Article25.htm, two pages.
Visual Acuity of the Human Eye, 3 pages, downloaded from http://www.ndt.ed.org/EductationResources/CommunityCollege/PenetrantTest/Introduction/visualacuity.htm.
V. Ryan, Annealing Metals, downloaded Nov. 2, 2010 from http://www.technologystudent.com/equip1/heat3.htm, 2 pages.
p. 301 of Metals Handbook 8th Edition, vol. 8, Metallography, Structures and Phase Diagrams,1973.
Annual Book of ASTM Standards 2000, vol. 02.01, Section 2, p. 876.
p. 171 of Metals Handbook 8th Edition, vol. 8, Metallography, Structures and Phase Diagrams,1973.
pp. 641, 642 and 411 of Metals Handbook® Ninth Edition, vol. 9, Metallography and Microstructures, 1985.
Restriction/Election mailed in co-pending U.S. Appl. No. 11/573,638 on Apr. 13, 2011.
pp. 1, 3, 5, 15 and 16 of Terms and Definition of Metals Handbook 9th Edition, vol. 9, Metallography and Microstructures, American Society for Metals, previously submitted as Exhibit E.
pp. 257-259 of ASM Specialty Handbook, Copper and Copper Alloys, ASM International, previously submitted as Exhibit F.
p. 277 of Degarmo, E. Paul; Black, J T.; Kohser, Ronald A. (2003), Materials and Processes in Manufacturing 9th edition), attached hereto as Exhibit G.
pp. 277, 278, 365, 373, 374, 383, 384, 407 and 408 of Degarmo, E. Paul; Black, J T.; Kohser, Ronald A., Materials and Processes in Manufacturing 9th edition (2003), John Wiley & Sons, Inc., filed in related U.S. Appl. No. 11/573,640 as Exhibit J.
pp. 9 and 15 of Terms and Definition of Metals Handbook 9th Edition, vol. 9, Metallography and Microstructures, American Society for Metals, filed in related U.S. Appl. No. 11/573,640 as Exhibit I.
E. Paul Degarmo, Materials and Processes in Manufacturing 276-295 (John Wiley & Sons, Inc. 9th Ed. 2003), filed herewith as Exhibit A1.
"Casting and Solidification Process," dated Jan. 9, 2010, at http://classes.engr.oregonstate.edu/mime/winter2010/ie337-001/Laboratories/5.Solidification%20Lab.pdf, downloaded Nov. 23, 2011, three pages, filed herewith as Exhibit B1.
E. Paul Degarmo, Materials and Processes in Manufacturing 82-85 (John Wiley & Sons, Inc. 9th Ed. 2003), filed herewith as Exhibit C1.
Patent Abstracts of Japan English Abstract corresponding to JP 2000/119775, filed herewith as Exhibit D1.
Office Action issued in co-pending U.S. Appl. No. 11/573,640, mailed Feb. 25, 2010.
Exhibit A2, filed in a co-pending related application, Metals Handbook 8th Ed., vol. 7, Atlas of Microstructures of Industrial Alloys 280 (American Society for Metals 1972).
Exhibit B2, filed in a co-pending related application, Metals Handbook 8th Ed., vol. 8, Metallography, Structures and Phase Diagrams 171 (American Society for Metals 1973), filed May 1, 2012 as NPL19.
Office Action issued in co-pending related U.S. Appl. No. 12/088,822 on Mar. 21, 2013.

(56) References Cited

OTHER PUBLICATIONS

Gubner, Rolf et al., Grain Boundary Corrosion of Copper Canister Weld Material, TR-06-01 (Svensk Kämbränslehantering AB 2006).
ASM Specialty Handbook: Copper and Copper Alloys, pp. 1-9 (ASM International 2001).
Procedures: Copper Welding, at http://www.brazing.com/techguide/procedures/copper_welding.asp (downloaded Jun. 13, 2012, six pages.
Metals Handbook® Ninth Edition, vol. 9, Metallography and Microstructures 155 and 408 (American Society for Metals 1985).
International Search Report issued in related application No. PCT/JP2005/018107, completed Dec. 13, 2005 and mailed Dec. 20, 2005.
Metals Handbook 290 (8th Edition 1972), filed in related application as Exhibit C3.
ASM Specialty Handbook® Copper and Copper Alloys 243-246 (2001), filed in related application as Exhibit E3.
Materials Mechanical Size Effects: a Review, 23 Materials Technology 193-209 (2008), filed in related as Exhibit F3.
N. J. Petch, The Cleavage Strength of Polycrystals, Journal of The Iron and Steel Institute, May 1953, pp. 25-28.
E.O. Hall, The Deformation and Ageing of Mild Steel, Mar. 1951, pp. 747-753.
Winfried Reif, Kornfeinung von Aluminium-, Blei-, Zinn-, Kupfer- und Nickellegierungen-ein Überblick, Giesserei 76, 1989, Nr.2, pp. 41-47.
F. Romankiewicz, Kornfeinung von Kupferlegierungen, Metall, 48. Jahrgang, Nr. 11/94, pp. 865-871.
Ferdynand Romankiewicz, Einfluβ einer Kornfeinung mitZirconium auf Erstarrungsmorphologie, Speisungsvermögen und Festigkeitseigenschaften von Messing CuZn30 und Siliciummessing CuZn15Si4, 39, Jahrgang 1987 Heft 1, pp. 25-33.
R. Mannheim, Untersuchung der Kornfienung von Kupfer-Zinn-Legierungen mit Zirconium und/oder Bor und Eisen sowie ihres Einflusses auf die mechanischen Eigenschaften, Giessereiforschung 40 1998 Nr. 1, pp. 1-16.
O. Bustos, Estudio de la combinanción de los procesos de afinamiento de grano de colada y filtrado en latones, Rev. Metal. Madrid, 35 (4), 1999, pp. 222-232.
A. Couture J.O. Edwards, Kornfeinung von Kupfer-Sandguβlegierungen und ihr Einfluβ auf die Güteeigenschaften, Giesserei-Praxis, Nr.21/1974, pp. 425-435.
M. Sadayappan, Fading of Grain Refinement in Leaded Yellow Brass (C85800) and SeBiLOY III (C89550, EnviroBrass III), AFS Transactions 01-116, 2001 American Foundry Society, pp. 705-713.
D. Cousineau, Grain Refinement of Permanent Mold Cast Copper-Base Alloys, AFS Transactions 02-108, 2002 American Foundry Society, pp. 505-514.

J.P. Thomson, Evaluation of Grain Rfinement of Leaded Yellow Brass (C85800) and EnviroBrass III (C89550) using Thermal Analysis, AFS Transactions 2003, pp. 417-434.
F.A. Fasoyinu, Effects of Grain Refinement on Hot Tear Resistance and Shrinkage Characteristics of Permanent Mold Cast Yellow Brass (C85800), pp. 327-337. (1998).
M. Sadayappan, Fading of Grain Refinement in Permanent Mold Cast Copper Alloys, AFS Transactions 2004 ® American Foundry Society, Des Plaines IL USA, pp. 521-526.
Prof. Dr.-Ing. W. Reif, A New Grain Refiner for Copper-Zinc Alloys containing 25-42%Zinc, Metall 41. Jahrgang Heft Nov. 11, 1987, pp. 1131-1137.
M. Sadayappan, GrainRefinement of Copper Base Alloys, vol. 1-Plenary Lectures/Movement of Copper and Industry Outlook/Copper Applications and Fabrication, 1999, pp. 279-291.
M. Sadayappan, Grain Refinement of Permanent Mold Cast Silicon Brass, Silicon Bronze and Red Brass, AFS Transactions, pp. 337-342. (1999).
A. Couture, Grain Refinement of Sand Cast Bronzes and its Influence on Their Properties, AFS Cast Metals Research Journal, Mar. 1974, pp. 1-5.
M. Sadayappan, Grain Refinement Studies on Leaded and Bi/Se Modified Yellow Brasses, pp. 45-58. (2001).
M. Sahoo, An Overview of ICA-Funded Research and Development at MTL/Canmet, pp. 1-12. (1999).
International Search Report issued in related application PCT/JP2005/008662, completed Jul. 21, 2005 and mailed Aug. 9, 2005.
Office Action issued in corresponding Brazilian patent application PI0509025-3 on Jul. 16, 2013 (no translation available).
ASM Specialty Handbook, Copper and Copper Alloys, 2001, pp. 213-215, "Forging and Extrusion.".
ASM Specialty Handbook, Copper and Copper Alloys, 2001, pp. 242-247, "Heat Treating."
Metals Handbook, 8th Edition, 1973, p. 169, "Solidification Structures of Copper Alloy Ingots."
Metals Handbook, vol. 9, Metallography and Microstructures, 1985, pp. 2, 5, 8, 9 and 15.
Final Office Action issued in co-pending related U.S. Appl. No. 10/596,849 on Jun. 26, 2014.
Flood, S. C. et al., "Columnar to Equiaxed Transition," published in Metal Handbook, vol. 15th, 9th Edition, pp. i,ii 130-133.
Handbook of Workability and Process Design, G.E. Dieter, H.A. Kuhn, and S.L. Semiatin, etditors, p. 35-44, DOI:101361/hwpd2003po35, Chapter 3, Evolution of Microstructure during Hot Working, ASM International, 2003.
Final Office Action issued in co-pending related U.S. Appl. No. 10/596,849 on Jul. 2, 2015.
International Search Report issued in corresponding application No. PCT/JP2005/014699, completed Sep. 2, 2005 and mailed Sep. 20, 2005.

* cited by examiner

FIG. 1
(A) 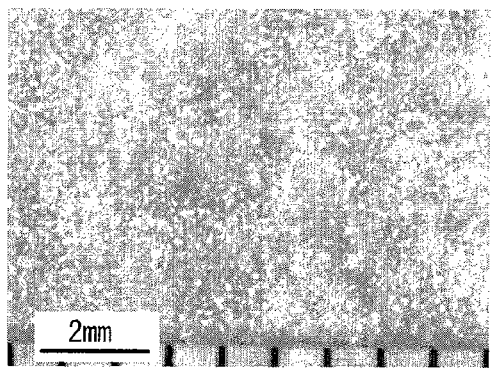 (B) 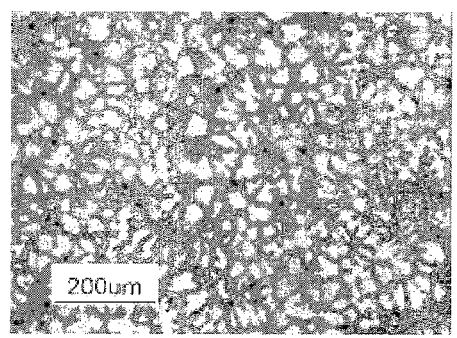
FIG. 2
(A) 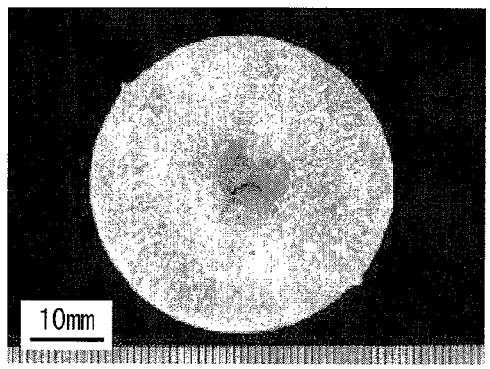 (B) 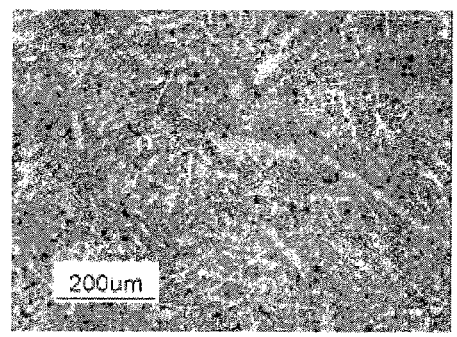

FIG. 7
(A)
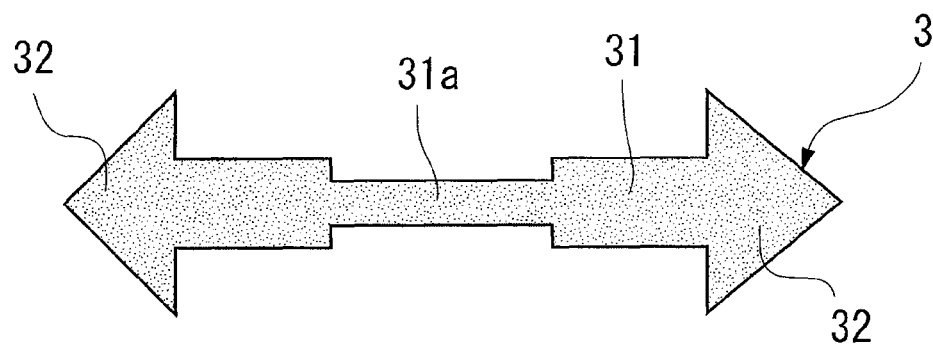
(B)
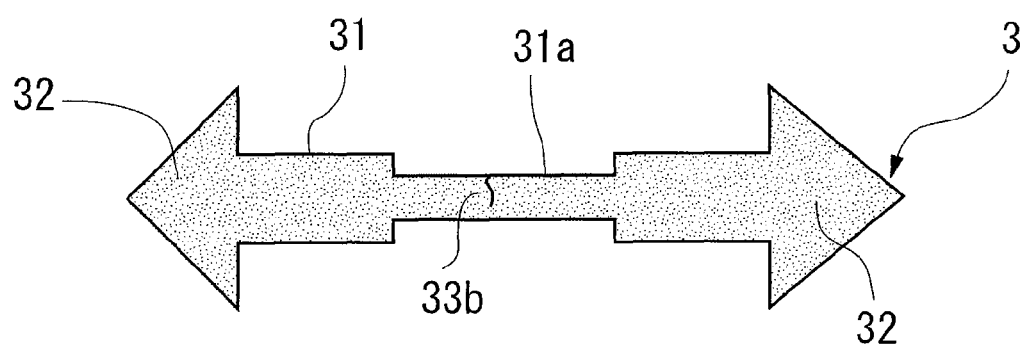
(C)
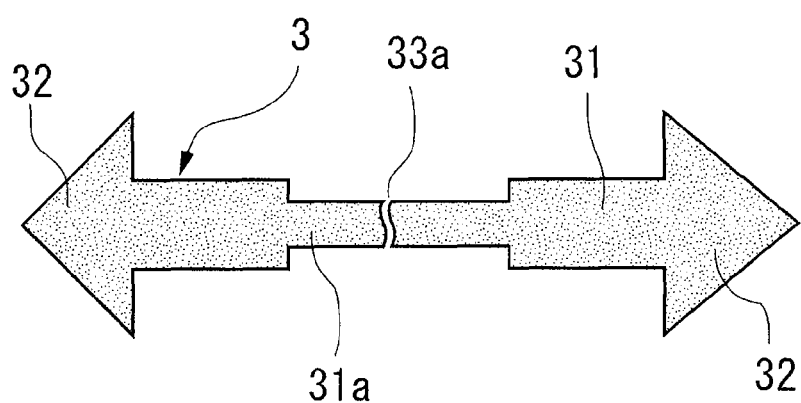

COPPER ALLOY CASTING HAVING EXCELLENT MACHINABILITY, STRENGTH, WEAR RESISTANCE AND CORROSION RESISTANCE AND METHOD OF CASTING THE SAME

This is a National Phase Application in the United States of International Patent Application No. PCT/JP2005/014697 filed Aug. 10, 2005, which claims priority on Japanese Patent Application No. 2004-233952, filed Aug. 10, 2004. The entire disclosures of the above patent applications are hereby incorporated by reference.

TECHNICAL FIELD

The present invention relates to a copper alloy casting, which has excellent machinability, strength, wear resistance and corrosion resistance and is preferably used as a water contact metal fitting (for example, water faucet of water supply pipe, valves, cocks, joints, flanges, in-house built device, water discharging tools, joint clip, boiler parts, or the like) used continuously or temporarily in contact with water (tap water or the like), friction engaging member (for example, bearing, gear, cylinder, bearing retainer, impeller, pump parts, bearing or the like) making a relative movement to a facing member (rotating shaft or the like) continuously or temporarily in contact with the facing member or the like, or the structural material thereof, and a method of casting the same.

BACKGROUND ART

A copper alloy casting used as a water contact metal fitting, friction engaging member, or the structural material thereof (half-finished products) needs to have high machinability and wear resistance as well as the strength and corrosion resistance. However, CAC406, CAC602 and CAC604 of JIS H5120, CAC406C of JIS H5121 or the like, which are generally used as the structural material of said copper alloy casting, are not satisfactory in the above-mentioned properties, castability or the like.

In the related art, it is well known that grain refinement is extremely effective in improving the strength, castability or the like of a copper alloy casting by removing dendrite structure, a typical structure of a casting.

Basically, the grains of a copper alloy are refined as follows: (A) the grains are refined during the melt-solidification of a copper alloy, or (B) the grains are refined by deforming such as rolling or the like, or heating the melt-solidified copper alloy (ingot such as slab or the like; casting such as die casting or the like; molten casting products or the like), in which stacking energy such as distortion energy or the like acts as a driving force. In both cases, Zr is known as an element contributing to the grain refinement effectively.

In the case of method (A), since the grain-refining effect of Zr during melt-solidification is considerably dependent upon the other elements and the contents thereof, the grains as refined as desired cannot be obtained. As a result, method (B) is commonly used, and the grains are refined by heating and then deforming a melt-solidified ingot, casting or the like.

JP-B-38-20467 discloses that the grains are further refined as the content of Zr increases; for instance, it discloses the measurement results that the mean grain size of a copper alloy containing Zr, P, and Ni, on which solution treatment is performed and then cold-working is performed at a working rate of 75%, is 280 μm when no Zr is contained, 170 μm when 0.05 mass % of Zr is contained), 50 when 0.13 mass % of Zr is contained, 29 μm when 0.22 mass % of Zr is contained, and 6 μm when 0.89 mass % of Zr is contained. In addition, JP-B-38-20467 suggests that the content of Zr should be in the range of 0.05 to 0.3 mass % in order to avoid a negative influence caused by the excessive addition of Zr.

Furthermore, JP-A-2004-100042 discloses that the mean grain size can be as fine as about 20 μm or less if a copper alloy, to which 0.15 to 0.5 mass % of Zr is added, is subject to solution treatment and then deformation process after casting.

Patent Document 1: JP-B-38-20467
Patent Document 2: JP-A-2004-100042

However, if a casting is heated and deformed to refine the grains like method (B), the manufacturing cost rises. Also, there is a casting, the shape of which makes a deformation process impossible. Therefore, it is preferable that the grains be refined while a copper alloy is being melt-solidified by method (A). However, in the case of method (A), as described above, since the grain-refining effect of Zr considerably depends on the other elements and the contents thereof during melt-solidification, when the content of Zr increases, it does not necessarily mean that the grains are refined as much as expected by the increased amount. In addition, since Zr has an extremely strong affinity to oxygen, when Zr is melted and added in the air, Zr is likely to be oxidized, and thus the yield of Zr decreases drastically. As a result, even when a manufactured casting contains a little amount of Zr, a large amount of Zr raw material needs to be charged upon pouring. On the other hand, if too much oxide is generated during melting, the oxide can be included into a molten alloy during pouring, thereby inducing casting defects. In order to prevent the oxide from generating, it can be considered that the raw materials are melted and cast under a vacuum or inert gas atmosphere. This method, however, raises the manufacturing cost. Furthermore, since Zr is an expensive element, it is preferable that the adding amount of Zr be suppressed as low as possible from an economic point of view.

Consequently, it is demanded that the content of Zr be made as low as possible and a copper alloy casting, the grains of which are refined at the stage of melt-solidification during casting, be developed.

DISCLOSURE OF THE INVENTION

The invention has been finalized in views of the drawbacks inherent to the copper alloy casting in the related art, and it is an advantage of the invention to provide a copper alloy casting having the considerably improved castability, machinability, strength, wear resistance and corrosion resistance by the grain refinement during melt-solidification which is preferably used as a water contact metal fitting, friction engaging member or the like, and a method of casting that manufactures the above-described copper alloy casting preferably.

The invention proposes the following copper alloy castings having excellent machinability, strength, ductility, wear resistance and corrosion resistance, and the following method of casting the same in order to achieve the above advantages.

That is, the invention proposes, firstly, a copper alloy casting with excellent machinability, strength, wear resistance and corrosion resistance (hereinafter referred to as 'first copper alloy casting') containing Sn: 0.5 to 15 mass % (preferably 2 to 10 mass %, more preferably 3 to 8 mass %, and optimally 4 to 7.5 mass %); Zr: 0.001 to 0.049 mass % (preferably 0.004 to 0.039 mass %, more preferably 0.006 to 0.029 mass %, and optimally 0.008 to 0.024 mass %); P: 0.01 to 0.35 mass % (preferably 0.02 to 0.19 mass %, more preferably 0.03 to 0.15 mass %, and optimally 0.035 to 0.12 mass %); one or more elements selected from Pb: 0.01 to 15 mass % (preferably 0.45 to 12 mass %, more preferably 1 to 10 mass %, and optimally 2 to 6 mass %), Bi: 0.01 to 15 mass % (preferably 0.45 to 12 mass %, more preferably 0.6 to 10 mass %, and optimally 1 to 4 mass %), Se: 0.01 to 1.2 mass % (preferably 0.07 to 1 mass %, more preferably 0.1 to 0.8 mass %, and optimally 0.2 to 0.7 mass %), and Te: 0.05 to 1.2 mass % (preferably 0.07 to 1 mass %, more preferably 0.1 to 0.8 mass %, and optimally 0.2 to 0.7 mass %); and Cu: 73 mass % or more serving as a remainder (preferably 73 to 92 mass %, more preferably 73 to 91 mass %, further more preferably 73.5 to 89 mass %, and optimally 75 to 84 mass %) and satisfying the following conditions (1) to (5). It is preferable that the first copper alloy casting further satisfy the following conditions (7) to (13) in addition to the above conditions.

The invention proposes, secondly, a copper alloy casting with excellent machinability, strength, wear resistance and corrosion resistance (hereinafter referred to as 'second copper alloy casting') further containing one or more elements selected from Al, Mn and Mg in addition to the composition of the first copper alloy casting, that is, containing Sn: 0.5 to 15 mass % (preferably 2 to 10 mass %, more preferably 3 to 8 mass %, and optimally 4 to 7.5 mass %); Zr: 0.001 to 0.049 mass % (preferably 0.004 to 0.039 mass %, more preferably 0.006 to 0.029 mass %, and optimally 0.008 to 0.024 mass %); P: 0.01 to 0.35 mass % (preferably 0.02 to 0.19 mass %, more preferably 0.03 to 0.15 mass %, and optimally 0.035 to 0.12 mass %); one or more elements selected from Pb: 0.01 to 15 mass % (preferably 0.45 to 12 mass %, more preferably 1 to 10 mass %, and optimally 2 to 6 mass %), Bi: 0.01 to 15 mass % (preferably 0.45 to 12 mass %, more preferably 0.6 to 10 mass %, and optimally 1 to 4 mass %), Se: 0.01 to 1.2 mass % (preferably 0.07 to 1 mass %, more preferably 0.1 to 0.8 mass %, and optimally 0.2 to 0.7 mass %), and Te: 0.05 to 1.2 mass % (preferably 0.07 to 1 mass %, more preferably 0.1 to 0.8 mass %, and optimally 0.2 to 0.7 mass %); one or more elements selected from Al: 0.005 to 0.5 mass % (preferably 0.005 to 0.2 mass %, and more preferably 0.01 to 0.1 mass %), Mn: 0.01 to 0.5 mass % (preferably 0.03 to 0.3 mass %, and more preferably 0.05 to 0.2 mass %), and Mg: 0.001 to 0.2 mass % (preferably 0.002 to 0.15 mass %, and more preferably 0.005 to 0.1 mass %); and Cu: 73 mass % or more serving as a remainder (preferably 73 to 92 mass %, more preferably 73 to 91 mass %, further more preferably 73.5 to 89 mass %, and optimally 75 to 84 mass %) and satisfying the following conditions (1) to (5). It is preferable that the second copper alloy casting further satisfy the following conditions (7) to (13) in addition to the above conditions.

The invention proposes, thirdly, a copper alloy casting with excellent machinability, strength, wear resistance and corrosion resistance (hereinafter referred to as 'third copper alloy casting') further containing Zn in addition to the composition of the first copper alloy casting, that is, containing Sn: 0.5 to 15 mass % (preferably 2 to 10 mass %, more preferably 3 to 8 mass %, and optimally 4 to 7.5 mass %); Zr: 0.001 to 0.049 mass % (preferably 0.004 to 0.039 mass %, more preferably 0.006 to 0.029 mass %, and optimally 0.008 to 0.024 mass %); P: 0.01 to 0.35 mass % (preferably 0.02 to 0.19 mass %, more preferably 0.03 to 0.15 mass %, and optimally 0.035 to 0.12 mass %); one or more elements selected from Pb: 0.01 to 15 mass % (preferably 0.45 to 12 mass %, more preferably 1 to 10 mass %, and optimally 2 to 6 mass %), Bi: 0.01 to 15 mass % (preferably 0.45 to 12 mass %, more preferably 0.6 to 10 mass %, and optimally 1 to 4 mass %), Se: 0.01 to 1.2 mass % (preferably 0.07 to 1 mass %, more preferably 0.1 to 0.8 mass %, and optimally 0.2 to 0.7 mass %), and Te: 0.05 to 1.2 mass % (preferably 0.07 to 1 mass %, more preferably 0.1 to 0.8 mass %, and optimally 0.2 to 0.7 mass %); Zn: 18 mass % or less (preferably 0.01 to 17.5 mass %, more preferably 3 to 17 mass %, and optimally 5 to 16 mass %); and Cu: 73 mass % or more serving as a remainder (preferably 73 to 92 mass %, more preferably 73 to 91 mass %, further more preferably 73.5 to 89 mass %, and optimally 75 to 84 mass %) and satisfying the following conditions (1) to (6). It is preferable that the third copper alloy casting further satisfy the following conditions (7) to (13) in addition to the above conditions.

The invention proposes, fourthly, a copper alloy casting with excellent machinability, strength, wear resistance and corrosion resistance (hereinafter referred to as 'fourth copper alloy casting') further containing one or more element selected from Al, Mn, and Mg in addition to the composition of the third copper alloy casting, that is, containing Sn: 0.5 to 15 mass % (preferably 2 to 10 mass %, more preferably 3 to 8 mass %, and optimally 4 to 7.5 mass %); Zr: 0.001 to 0.049 mass % (preferably 0.004 to 0.039 mass %, more preferably 0.006 to 0.029 mass %, and optimally 0.008 to 0.024 mass %); P: 0.01 to 0.35 mass % (preferably 0.02 to 0.19 mass %, more preferably 0.03 to 0.15 mass %, and optimally 0.035 to 0.12 mass %); one or more elements selected from Pb: 0.01 to 15 mass % (preferably 0.45 to 12 mass %, more preferably 1 to 10 mass %, and optimally 2 to 6 mass %), Bi: 0.01 to 15 mass % (preferably 0.45 to 12 mass %, more preferably 0.6 to 10 mass %, and optimally 1 to 4 mass %), Se: 0.01 to 1.2 mass % (preferably 0.07 to 1 mass %, more preferably 0.1 to 0.8 mass %, and optimally 0.2 to 0.7 mass %), and Te: 0.05 to 1.2 mass % (preferably 0.07 to 1 mass %, more preferably 0.1 to 0.8 mass %, and optimally 0.2 to 0.7 mass %); Zn: 18 mass % or less (preferably 0.01 to 17.5 mass %, more preferably 3 to 17 mass %, and optimally 5 to 16 mass %); one or more elements selected from Al: 0.005 to 0.5 mass % (preferably 0.005 to 0.2 mass %, and more preferably 0.01 to 0.1 mass %), Mn: 0.01 to 0.5 mass % (preferably 0.03 to 0.3 mass %, and more preferably 0.05 to 0.2 mass %), and Mg: 0.001 to 0.2 mass % (preferably 0.002 to 0.15 mass %, and more preferably 0.005 to 0.1 mass %); and Cu: 73 mass % or more serving as a remainder (preferably 73 to 92 mass %, more preferably 73 to 91 mass %, further more preferably 73.5 to 89 mass %, and optimally 75 to 84 mass %) and satisfying the following conditions (1) to (6). It is preferable that the fourth copper alloy casting further satisfy the following conditions (7) to (13) in addition to the above conditions.

The invention proposes, fifthly, a copper alloy casting with excellent machinability, strength, wear resistance and corrosion resistance (hereinafter referred to as 'fifth copper alloy casting') further containing As and/or Sb in addition to the composition of the third copper alloy casting, that is, containing Sn: 0.5 to 15 mass % (preferably 2 to 10 mass %, more preferably 3 to 8 mass %, and optimally 4 to 7.5 mass %); Zr: 0.001 to 0.049 mass % (preferably 0.004 to 0.039 mass %, more preferably 0.006 to 0.029 mass %, and optimally 0.008 to 0.024 mass %); P: 0.01 to 0.35 mass % (preferably 0.02 to 0.19 mass %, more preferably 0.03 to 0.15 mass %, and optimally 0.035 to 0.12 mass %); one or more elements selected from Pb: 0.01 to 15 mass % (preferably 0.45 to 12 mass %, more preferably 1 to 10 mass %, and optimally 2 to 6 mass %), Bi: 0.01 to 15 mass % (preferably 0.45 to 12 mass %, more preferably 0.6 to 10 mass %, and optimally 1 to 4 mass %), Se: 0.01 to 1.2 mass % (preferably 0.07 to 1 mass %, more preferably 0.1 to 0.8 mass %, and optimally 0.2 to 0.7 mass %), and Te: 0.05 to 1.2 mass % (preferably 0.07 to 1 mass %, more preferably 0.1 to 0.8 mass %, and optimally 0.2 to 0.7 mass %); Zn: 18 mass % or less (preferably 0.01 to 17.5 mass %, more preferably 3 to 17 mass %, and optimally 5 to 16 mass %); As: 0.02 to 0.2 mass % (preferably 0.04 to 0.12 mass %) and/or Sb: 0.02 to 0.2 mass % (preferably 0.04 to 0.12 mass %); and Cu: 73 mass % or more serving as a remainder (preferably 73 to 92 mass %, more preferably 73 to 91 mass %, furthermore 73.5 to 89 mass %, and optimally 75 to 84 mass %) and satisfying the following conditions (1) to (6). It is preferable that the fifth copper alloy casting further satisfy the following conditions (7) to (13) in addition to the above conditions.

The invention proposes, sixthly, a copper alloy casting with excellent machinability, strength, wear resistance and corrosion resistance (hereinafter referred to as 'sixth copper alloy casting') further containing one or more element selected from Al, Mn and Mg and As and/or Sb in addition to the composition of the third copper alloy casting, that is, containing Sn: 0.5 to 15 mass % (preferably 2 to 10 mass %, more preferably 3 to 8 mass %, and optimally 4 to 7.5 mass %); Zr: 0.001 to 0.049 mass % (preferably 0.004 to 0.039 mass %, more preferably 0.006 to 0.029 mass %, and optimally 0.008 to 0.024 mass %); P: 0.01 to 0.35 mass % (preferably 0.02 to 0.19 mass %, more preferably 0.03 to 0.15 mass %, and optimally 0.035 to 0.12 mass %); one or more elements selected from Pb: 0.01 to 15 mass % (preferably 0.45 to 12 mass %, more preferably 1 to 10 mass %, and optimally 2 to 6 mass %), Bi: 0.01 to 15 mass % (preferably 0.45 to 12 mass %, more preferably 0.6 to 10 mass %, and optimally 1 to 4 mass %), Se: 0.01 to 1.2 mass % (preferably 0.07 to 1 mass %, more preferably 0.1 to 0.8 mass %, and optimally 0.2 to 0.7 mass %), and Te: 0.05 to 1.2 mass % (preferably 0.07 to 1 mass %, more preferably 0.1 to 0.8 mass %, and optimally 0.2 to 0.7 mass %); Zn: 18 mass % or less (preferably 0.01 to 17.5 mass %, more preferably 3 to 17 mass %, and optimally 5 to 16 mass %); one or more elements selected from Al: 0.005 to 0.5 mass % (preferably 0.005 to 0.2 mass %, and more preferably 0.01 to 0.1 mass %), Mn: 0.01 to 0.5 mass % (preferably 0.03 to 0.3 mass %, and more preferably 0.05 to 0.2 mass %), and Mg: 0.001 to 0.2 mass % (preferably 0.002 to 0.15 mass %, and more preferably 0.005 to 0.1 mass %); As: 0.02 to 0.2 mass % (preferably 0.04 to 0.12 mass %) and/or Sb: 0.02 to 0.2 mass % (preferably 0.04 to 0.12 mass %); and Cu: 73 mass % or more serving as a remainder (preferably 73 to 92 mass %, more preferably 73 to 91 mass %, further more preferably 73.5 to 89 mass %, and optimally 75 to 84 mass %) and satisfying the following conditions (1) to (6). It is preferable that the sixth copper alloy casting further satisfy the following conditions (7) to (13) in addition to the above conditions.

Meanwhile, in the present description, [a] indicates the content value of an element 'a', and the content of the element 'a' is expressed as [a] mass %. For example, the content of Cu is expressed as [Cu] mass %.

(1) $f1=[P]/[Zr]=0.5$ to 100 (preferably $f1=0.7$ to 25, more preferably $f1=1.1$ to 15, and optimally $f1=1.5$ to 10)

(2) $f2=([Zn]+3[Sn])/[Zr]=300$ to 15000 (preferably $f2=500$ to 7000, more preferably $f2=800$ to 4000, and optimally $f2=1100$ to 3000). In the first and second copper alloy castings, $[Zn]=0$, and thus $f2=3[Sn]/[Zr]$.

(3) $f3=([Zn]+3[Sn])/[P]=40$ to 2500 (preferably $f3=100$ to 1600, more preferably $f3=150$ to 1200, and optimally $f3=220$ to 800). In the first and second copper alloy castings, $[Zn]=0$, and thus $f3=3[Sn]/[P]$.

(4) The total content of α-phase, γ-phase and δ-phase should be 95% or more (preferably 99% or more). Meanwhile, the area ratio of each phase is measured by image analysis, specifically, by expressing the structure of a copper alloy casting, 200 times magnified by an optical microscope, in the binary system with an image processing software 'WinROOF' (manufactured by Tech-Jam Co., Ltd.), and the area ratio is the average value of the area ratios measured at three locations.

(5) The mean grain size should be 300 μm or less (preferably 200 μm or less, more preferably 100 μm or less) in the macrostructure (60 μm or less in the microstructure) at melt-solidification. In this case, the mean grain size in the macrostructure (or microstructure) at melt-solidification means the average value of the grain sizes in the macrostructure (or microstructure) of a casting, welding or fusing, on which no deformation process (extrusion, rolling or the like) or heating treatment is performed after melt-solidification, including various conventional casting methods such as permanent mold casting, sand casting, horizontal continuous casting, upward (upcast), semi-solid metal casting, semi-solid metal forging, molten alloy forging or the like. Meanwhile, in the present description, a 'casting' means a product, all or part of which is melted and solidified, and includes the castings such as ingot, slab, billet for rolling or extrusion; sand casting, permanent mold casting, low-pressure casting, die casting, lost wax, semi-solid metal molding, semi-solid casting (for example, thixo-casting, rheo-casting), squeeze, centrifugal casting, continuous casting (for example, rod, hollow rod, irregular-shaped rod, irregular-shaped hollow rod, coil material, wire or the like manufactured by horizontal continuous casting, upward, upcast), casting manufactured by molten alloy forging (direct forging), thermal spraying, built-up, lining and overlay. In addition, welding is also considered as casting in a broad sense, since part of mother material is melted and solidified before being welded.

(6) $f4=[Zn]+3[Sn]=10$ to 43 (preferably $f4=16$ to 42, more preferably $f4=21$ to 40, and optimally $f4=25$ to 38).

(7) $f5=[Cu]-0.5[Sn]-3[P]+0.5([Pb]+[Bi]+[Se]+[Te])-0.5([As]+[Sb])-1.8[Al]+[Mn]+[Mg]=60$ to 90 (preferably $f5=72$ to 89, more preferably $f5=72.5$ to 88, and optimally $f5=73$ to 85). In the above equation, an element 'a' that is not contained is expressed as $[a]=0$.

(8) The primary crystal that appears during melt-solidification is α-phase.

(9) During melt-solidification, peritectic reaction occurs.

(10) During melt-solidification, a crystal structure, in which dendrite network is divided, is formed.

(11) The two-dimensional shape of the grains during melt-solidification is circular, substantially circular, oval, cross-like, acicular, or polygonal.

(12) α-phase is divided finely in the matrix, and δ-phase, γ-phase or high Sn-concentration part, which is generated by segregation, is distributed uniformly in the matrix.

(13) When Pb or Bi is contained, particles of Pb or Bi are uniform in diameter and are distributed uniformly in the matrix.

In the first to sixth copper alloy castings, Cu is a main element of the copper alloy composing the casting. When the content of Cu increases, the α-phase become easily obtainable and the corrosion resistance (dezincification corrosion resistance, stress corrosion cracking resistance) and mechanical properties are improved. However, an excessive addition of Cu deters the grain refinement. Therefore, the content of Cu is set as the remainder. Furthermore, depending on the mixing ratio to Sn (and Zn), it is preferable that the minimum value of the Cu content range be determined to secure more stable corrosion resistance and erosion resistance, and that the maximum value of the Cu content range be determined to secure higher strength and wear resistance. Considering the above facts, the content of Cu needs to be 73 mass % or more, preferably in the range of 73 to 92 mass %, more preferably 73 to 91 mass %, further more preferably 73.5 to 89 mass %, and optimally 75 to 84 mass %.

In the first to sixth copper alloy castings, Sn is contained mainly to improve the corrosion resistance. When 0.5 mass % or more of Sn is contained, the corrosion resistance, erosion resistance, wear resistance and strength are improved. However, when the content of Sn reaches 15 mass %, the above effect is saturated. When the content of Sn exceeds 15 mass %, the ductility and castability rather deteriorate, and casting defects such as crack, shrinkage cavity, porosity or the like are induced. In addition, Sn works to widen the composition range, in which peritectic reaction (an effective method of refining the grains during melt-solidification) is generated, and thus peritectic reaction occurs in a wider range of Cu concentration at the actual production as the content of Sn increases. Considering the above facts, the content of Sn is preferably 2 mass % or more, more preferably 3 mass % or more, and optimally 4 mass % or more. On the other hand, if the content of Sn exceeds 15 mass %, though depending on the mixing ratio to Cu and Zn, δ-phase (and γ-phase), which is a hard phase having a higher Sn concentration than the matrix (α-phase), is generated excessively (more than 20% by area ratio), and the corrosion resistance is likely to deteriorate. Furthermore, although depending on the mixing ratio to Cu (Cu and Zn in case of the third to sixth copper alloy castings), if the concentration of Sn becomes extremely high, Sn is segregated remarkably, and the temperature range of solidification is widened as the amount of Sn increases, thereby impairing the castability. Considering the above facts, in order to secure the appropriate content of the δ-phase (and the γ-phase) as well, the content of Sn needs to be in the range of 0.5 to 15 mass %, preferably 2 to 10 mass %, more preferably 3 to 8 mass %, and optimally 4 to 7.5 mass %. Then, the amount of the δ-phase (and the γ-phase) generated falls in the appropriate range (20% or less by area ratio).

In the first to sixth copper alloy castings, Zr and P are added together in order to refine the grains of the copper alloy, particularly during melt-solidification. That is, though a single addition of either Zr or P can refine the grains of the copper alloy only slightly like the other additive elements, if Zr and P are added together, Zr and P works to refine the grains of the copper alloy effectively.

Such grain refining effect is achieved when the content of Zr is 0.001 mass % or more, remarkably when the content of Zr is 0.004 mass % or more, more remarkably when the content of Zr is 0.006 mass % or more, and extremely remarkably when the content of Zr is 0.008 mass % or more. With respect to P, it is achieved when the content of P is 0.01 mass % or more, remarkably when the content of P is 0.02 mass % or more, more remarkably when the content of P is 0.03 mass % or more, and extremely remarkably when the content of P is 0.035 mass %.

Meanwhile, if the amount of Zr reaches 0.049 mass %, and the amount of P reaches 0.35 mass %, the effect of the co-addition of Zr and P to refine the grains saturates completely, regardless of a type of any other component element and the content thereof. Therefore, the amount of Zr and P required to refine the grains effectively is 0.049 mass % or less for Zr and 0.35 mass % or less for P. If the adding amounts of Zr and P are as small as defined in the above ranges, the properties obtained by the other component elements are not impaired. Rather, high Sn-concentrated part generated by segregation can be distributed uniformly in the matrix due to the grain refinement, instead of being tangled at a certain location. At the same time, it is possible to make the molten alloy in a state where the cutting property-improving elements that are not subject to solid solution such as Pb, Bi or the like are taken most advantage of; that is, the state where the particles of Pb, Bi or the like are small and uniform in diameter and distributed and dispersed uniformly in the matrix. As a result, it is possible to prevent casting crack and to obtain a robust casting having little amount of porosity, shrinkage cavity, blowhole, and/or microporosity. In addition, the workability of cold drawing performed after the casting is also improved, and thus the properties of the alloy are further improved.

Since Zr has an extremely strong affinity to oxygen, when Zr is melted in the air or a scrap material is used as raw material, Zr is likely to form oxide or sulfide. Therefore, if an excessive amount of Zr is added, the viscosity of the molten alloy increases; casting defects are induced by the inclusion or the like of the oxide and/or sulfide; and blowhole or microporosity is highly likely to occur. In order to avoid the above problems, it is considered that Zr is melted and cast under the vacuum or completely inert gas atmosphere. However, such method lacks generality and the manufacturing cost of a copper alloy, to which Zr is added only as a grain refiner, rises drastically. Considering the above facts, the content of Zr, not in the form of oxide nor sulfide, is preferably 0.039 mass % or less, more preferably 0.029 mass % or less, and optimally 0.024 mass % or less. In addition, if the amount of Zr is in the above ranges, even when the casting is melted in the air as a recycled material, the less amount of Zr oxide and/or sulfide is generated, and therefore, robust castings of the first to eighth copper alloy, recomposed of fine grains, can be obtainable. Meanwhile, the grains are not necessarily refined further even if more than 0.029 mass % of Zr is added, and the grain-refining effect almost saturates when more than 0.039 mass % of Zr is added.

From the above facts, taking into account that a small amount of Zr is added from an industrial viewpoint, the amount of Zr needs to be in the range of 0.001 to 0.049 mass %, preferably 0.004 to 0.039 mass %, more preferably 0.006 to 0.029 mass %, and optimally 0.008 to 0.024 mass %.

Even though P is added with Zr to refine the grains as described above, P also has an influence on the corrosion resistance, castability or the like. Therefore, considering that the minimum value of the adding amount range of P has an influence on the corrosion resistance, castability or the like in addition to the grain-refining function induced by the co-addition with Zr, and that the maximum value of the amount range of P has an influence on the ductility or the like, the amount of P needs to be in the range of 0.01 to 0.35 mass %, preferably 0.02 to 0.19 mass %, more preferably 0.03 to 0.15 mass %, and optimally 0.035 to 0.12 mass %.

In order for the co-addition of Zr and P to show its grain refining effect, it is also required that the contents of Zr and P satisfy the condition (1), as well as the contents of Zr and P be determined in the above ranges. The grains are refined when the nucleation rate of the α-phase primary crystal, which is crystallized from the molten liquid, is much faster than the grain growth rate of the dendrite crystal. In order to induce such phenomenon, it is also required to consider the co-addition ratio of Zr and P (f1=[P]/[Zr]) as well as to determine the amounts of Zr and P individually. If each content of Zr and P is determined in a proper range so as to have a proper co-addition ratio, the co-addition and mutual action of Zr and P can remarkably facilitate the nucleation of the α-phase primary crystal, and thus, the nucleation radio of the a-phase becomes much faster than that of the grain growth of the dendrite crystal. When the contents of Zr and P are in the proper ranges and the co-addition ratio of P to Zr ([P]/[Zr]) is stoichiometric, an intermetallic compound of Zr and P (for example, ZrP, $ZrP_{1-x}$) are generated in the a-phase crystals by adding about several tens ppm of Zr, and the nucleation rate of the α-phase is increased when the value f1 of [P]/[Zr] becomes in the range of 0.5 to 100; remarkably increased when f1 becomes in the range of 0.7 to 25; more remarkably when f1 becomes in the range of 1.1 to 15; and further more remarkably when f1 becomes in the range of 1.5 to 10. That is, f1, the co-addition ratio of Zr and P, is an important factor for grain refinement, and if f1 is in the above range, the nucleation rate becomes much faster than the grain growth rate during melt-solidification. In addition, the co-addition amount ratios of Zr and P to Sn (Sn and Zn when Zn is contained) (f2= ([Zn]+3[Sn])/[Zr] and f3=([Zn]+3[Sn])/[P]) are also very important factors for grain refinement. Therefore, it is required that the above co-addition amount ratios be considered to satisfy the conditions (2) and (3).

As the melt-solidification proceeds and the ratio of solid phase increases, grains grow continuously and start to combine with each other in some parts. Thus, generally, the α-phase grains become larger. In this case, if peritectic reaction occurs while the molten material is solidified, the molten liquid, which is not yet solidified, reacts with solid α-phase by solid-liquid reaction, and therefore, β-phase is generated while the α-phase diminishes. As a result, the β-phase surrounds the α-phase; the grain sizes of the α-phase grains decrease; and the shape of the α-phase grains become oval with the edges rounded off. If the solid phase becomes fine and oval, gas can be escaped easily; the casting obtained has a resistance to cracking accompanied by solidification shrinkage caused while the molten alloy is solidified; shrinkage proceeds smoothly; various properties such as strength, corrosion resistance or the like at the room temperature are improved. It is needless to say that, if the solid phase is fine and oval, the solid phase has a good flowability and becomes optimal for semi-solid metal solidifying method. In addition, if fine and oval solid phase and the liquid remain in the molten alloy at the final stage of solidification, the molten alloy can be sufficiently supplied to every corner of a mold, even for a complicatedly shaped casting. Therefore, a casting having an excellent shape, that is, a near net shape casting, can be obtained. Meanwhile, unlike the case of equilibrium state, the peritectic reaction occurs within a wider composition range than that of the equilibrium state in the actual production process. In this case, equations f4 and f5 play important roles, and the maximum value of f5 (the minimum value of f4) is related mainly with the grain size after melt-solidification and the criterion that determines whether the peritectic reaction occurs. The minimum value of f5 (the maximum value of f4) is related mainly with the crystal size after melt-solidification and the threshold value that determines whether the primary crystal is α-phase. As the values obtained from f5 and f4 are shifted from the above preferable range to the optimal range via more preferable range, the amount of the α-phase primary crystal increases; the peritectic reaction at a non-equilibrium state is generated more actively; and therefore, the grains obtained at the room temperature become smaller. Since f2 and f3 express the relationship between f4 and Zr, and f4 and P, respectively, it is needless to say that f2 and f3 are also important factors.

Such series of melt-solidification phenomena as described depend on the cooling rate. That is, in a rapid cooling performed at a cooling rate of $10^5$° C./second or faster, the grains are not refined since there is no time for nucleation. Conversely, in a slow cooling performed at a cooling rate of $10^{-3}$° C./second or slower, the grains are not refined, either since the grain growth or combination of grains is expedited. Furthermore, as the state approaches the equilibrium, the composition range, in which peritectic reaction occurs, becomes narrow. Therefore, it is preferable that the cooling rate at the melt-solidification stage be in the range of $10^{-2}$ to $10^{4}$° C./second and most desirably in the range of $10^{-1}$ to $10^{3}$° C./second. Even in the above cooling rate range, the composition range, in which the grains are refined, is widened as the cooling rate approaches the maximum. Thus, the grains are further refined.

In the first to sixth copper alloy castings, Sn has only a slight influence on the grain refinement if added alone. However, if added in the presence of Zr and P, Sn works on grain refinement remarkably. Sn improves the mechanical properties (strength or the like), corrosion resistance, and wear resistance, and also divides dendrite arms. In addition, Sn widens the composition range of Cu or Zn, in which peritectic reaction occurs, so as to induce peritectic reaction effectively. Sn also decreases the stacking fault energy of the alloy. As a result, the grains are granulated and refined more effectively. Sn shows the above functions particularly remarkably in the presence of Zr and P. Furthermore, the δ-phase and γ-phase (mainly the δ-phase) generated by the addition of Sn suppress the grain growth after melt-solidification and thus contribute to the grain refinement. The δ-phase (and γ-phase) is an area transformed from a high Sn-concentration part, and the high Sn-concentration parts are uniformly and finely dispersed at melt-solidification stage. Therefore, the δ-phase (and γ-phase) is also finely dispersed and suppresses the growth of α-phase grains at the high temperature range after solidification. Furthermore, since the δ-phase (and γ-phase) is finely dispersed, the corrosion resistance and wear resistance are also good. Therefore, in order for the co-addition of Zr and P to work on grain refinement effectively, the contents of Zr and P need to be determined in consideration of the mutual relationship between the contents of Zr and P, and said contents (of Zr and P) and Sn (and Zn) and thus, the conditions (2) and (3) in addition to (1) need to be satisfied. In other words, in order for the co-addition of Zr and P to work on grain refinement effectively, the content ratio of Zr to Sn and Zn, that is, f2 (=([Zn]+3[Sn])/[Zr]) and the content ratio of P to Sn and Zn, that is, f3 (=([Zn]+3[Sn])/[P]) are also important factors in addition to the mutual relationship between the contents of Zr and P. Thus it is required that f1=0.5 to 100; f2=300 to 15000; and f3=40 to 2500. In addition, the degree of grain refinement arising from the co-addition of Zr and P becomes larger when f1=0.7 to 25, f2=500 to 7000 and f3=100 to 1600; further larger when f1=1.1 to 15, f2=800 to 4000 and f3=150 to 1200; and extremely larger when f1=1.5 to 10, f2=1100 to 3000 and f3=220 to 800.

Similar to Sn, Zn contained in the third to sixth copper alloy castings generates the peritectic reaction that is a powerful method for refining the grains of an alloy during melt-solidification, decreases the stacking fault energy of an alloy, facilitates the flowability of the molten alloy, and lowers the melting point, as well as improves the corrosion resistance and mechanical properties (tensile strength, proof stress, impact strength, wear resistance, fatigue resistance or the like). In addition, Zn facilitates the grain refinement during melt-solidification and prevents the oxidation loss of Zr. However, if a large amount of Zn is added, the primary crystal during melt-solidification is β-phase, and thus the conditions (8) to (13) become difficult to be satisfied. Considering the above facts, the content of Zn needs to be 18 mass % or less, preferably in the range of 0.01 to 17.5 mass %, more preferably in the range of 3 to 17 mass %, and optimally in the range of 5 to 16 mass %.

In the first to sixth copper alloy castings, Pb, Bi, Se, and Te do not only improve the machinability as it is well known, but also improve the conformability and slidability against the counterpart member for friction engaging members such as bearing or the like, thereby improving the wear resistance of the casting. Particularly, such function becomes more effective if the condition (13) is satisfied, that is, if the particles of Pb or the like are small and uniform in size and are evenly dispersed in the matrix by grain refinement. The above effect of Pb, Bi, Se, and Te is obtainable by setting the content of each element to the aforesaid range. Generally, Pb, Bi, Se, and Te are added individually or in the combination of Pb and Te, Bi and Se, or Bi and Te. Meanwhile, if more than 15 mass % of Pb or Bi is added, the cutting surface is negatively affected; the ductility deteriorates considerably; and furthermore, the impact property and mechanical strength are impaired.

Meanwhile, Pb and Bi are not subject to solid solution at the room temperature and are present in the form of Pb and Bi particles. In addition, Pb and Bi are dispersed and exist among the solid phases in a granular shape in a molten state at the melt-solidification stage. Therefore, as the number of Pb and Bi particles increases, cracking is more likely to occur at the melt-solidification stage (due to tensile stress generated by solidification shrinkage). In addition, since Pb and Bi particles are present mainly at grain boundaries in a molten state after solidification, if the amount of the particles is large, high temperature cracking is highly likely to occur. In order to solve such problems, it is extremely effective to refine the grains so as to relieve the stress (and make the grain boundary area wider) and to make the Pb and Bi particles smaller and dispersed uniformly. In addition, Pb and Bi have a negative influence on the properties of a copper alloy except for machinability as described above. Since stress is centralized on the Pb and Bi particles, the room temperature ductility is also impaired (it is needless to say that, when the grains are large, the ductility is impaired synergistically). It is worth noting that the above problems can be solved by the grain refinement.

In the second, fifth, and sixth copper alloy castings, As and/or Sb are added mainly to improve the corrosion resistance (particularly, dezincification corrosion resistance). Even though the seawater resistance or corrosion resistance is improved when 0.02 mass % or more of Sb or As is added, in order to make such corrosion resistance-improving effect remarkable, it is preferable to add 0.04 mass % or more of Sb and/or As. Meanwhile, even when the adding amount of Sb or As exceeds 0.2 mass %, the corresponding effect to the increased amount is not obtained, and rather, the ductility deteriorates. In addition, the toxicity to human health becomes a problem. In view of such concerns, the adding amount of Sb and/or As needs to be 0.2 mass % or less, and preferably 0.12 mass % or less.

In the fourth and sixth copper alloy castings, Al, Mn, and Mg are added mainly to improve the strength and flowability of the molten alloy, to prevent oxidization and sulfurization, to improve erosion corrosion resistance under high speed of flow, and finally, to improve the wear resistance. In addition, Al forms a robust Al—Sn corrosion-resistant film on the surface of s casting so as to improve the wear resistance. Mn also forms a corrosion-resistant film with Sn. Meanwhile, scrap materials (wasted heat pipe and the like) are commonly used as part of copper alloy raw materials, and, generally, such scrap materials contain S-component (sulfuric component). If the S-component is contained in the molten alloy, Zr, a grain-refining element, is sulfurized and forms a sulfide, and thus the effective grain-refining effect induced by Zr is likely to be lost. In addition, the flowability of the molten alloy deteriorates, and thus casting defects such as blowhole, crack or the like are highly likely to occur. In addition to improving the corrosion resistance, Mg also improves the flowability of the molten alloy during casting even when a scrap material containing S-component is used as a raw material. In addition, Mg removes the S-component in the form of harmless MgS, and MgS does no harm to the corrosion resistance even if remained in the alloy. Mg also effectively prevents the deterioration of the corrosion resistance caused by the S-component contained in the raw material. Furthermore, Mg can effectively prevent the boundary corrosion, which is likely to occur by S-component contained in the raw material due to its tendency of being present at the grain boundary. Still furthermore, even though the effect is not as much as that of Mg, Al and Mn also works to remove the S-components contained in the molten alloy. In addition, when the amount of oxygen contained in the molten alloy is large, the grain refining effect of Zr is likely to be lost due to the formation of oxide. However, Mg, Al and Mn also prevent Zr from being oxidized. Considering the above facts, the contents of Al, Mn and Mg are determined to be in the above-mentioned ranges. When the concentration of S increases in the molten alloy, S is likely to consume Zr. However, if 0.001 mass % or more of Mg is contained in the molten alloy before the charging of Zr, the S-component in the molten alloy is removed or fixed in the form of MgS, therefore the above problem does not happen. On the contrary, if an excessive amount of Mg is contained, that is, if the content of Mg exceeds 0.2 mass %, it is likely that Mg oxidizes similar to Zr; the viscosity of the molten alloy increases; and the inclusion of oxide or the like generates casting defects. Therefore, when Mg is added, the amount needs to be determined in consideration of these points.

In order for the first to sixth copper alloy castings to secure sufficient corrosion resistance, wear resistance, strength or the like, it is required that each copper alloy casting have the above alloy composition and satisfy the condition (4). That is, the first to sixth copper alloy castings need to form a phase structure (metal structure), in which the total contents of the $\alpha$, $\gamma$ and $\delta$-phases (mainly the $\alpha$ and $\delta$-phases) occupy 95% or more (preferably 99% or more). However, if the content of the $\delta$-phase (and the $\gamma$-phase) is excessive, the corrosion resistance is impaired due to the occurrence of selective corrosion in the phases. In addition, although the $\delta$ and $\gamma$-phases improve the wear resistance and erosion corrosion resistance, the presence of $\delta$ and $\gamma$-phases can also be a cause of impairing ductility. Therefore, in order to secure the strength, wear resistance and ductility in a balanced manner while maintaining the corrosion resistance, the total content of the $\delta$ and $\gamma$-phases need to be in the range of 0 to 20% (preferably 0 to 10%, and more preferably 0. to 5%) by the area ratio. When the grains are refined by the co-addition of Zr and P, the $\delta$ and $\gamma$-phases are divided and spherically shaped inevitably, and the $\delta$ and $\gamma$-phases are distributed uniformly in a matrix, thereby considerably improving the machinability, mechanical properties and wear resistance (slidability). Particularly, if the particles of Pb or the like are uniform in diameter and are dispersed uniformly in the matrix as described in (13), the machinability (and slidability) can be improved remarkably.

In order for the first to sixth copper alloy castings to form the above-described phase structure and to satisfy the condition (5), it is preferable that the content of Sn be adjusted in consideration of the relationship with Cu and the other additional elements. That is, in order to realize the grain refinement more effectively, it is preferable that the content of Sn or the like be determined to satisfy the conditions (6) and (7) in addition to satisfy the conditions (1) to (3). Also, the minimum value of f4 ($=$[Zn]+3[Sn]) or the maximum value of f5 ($=$[Cu]−0.5[Sn]−3[P]+0.5([Pb]+[Bi]+[Se]+[Te])−0.5([As]+[Sb])−1.8[Al]+[Mn]+[Mg]) be set as described above in the relationship with Cu, one of the main elements, and with other elements involved in order to secure further excellent corrosion resistance (erosion corrosion resistance) and wear resistance. Meanwhile, considering the elongation, corrosion resistance and castability attributed to the δ and γ-phases, it is preferable that the maximum value of f4 or the minimum value of f5 be limited and set as described above. Upon securing the above properties, the concentration of Sn varies with the concentration of Cu.

In the first to sixth copper alloy castings, a high-quality casting is achieved when the condition (5) is satisfied by the grain refinement from the co-addition of Zr and P, that is, the mean grain size in the macrostructure during melt-solidification is 300 μm or less (preferably 200 μm or less, more preferably 100 μm or less and 60 μm or less in the microstructure). In addition, a casting manufactured by continuous casting methods such as horizontal continuous casting, upward (upcast) or the like can be provided at practical level. If the grains are not refined, at least one or more heat treatments is required to eliminate the dendrite structure that is unique to a casting; to prevent Sn from segregating; to divide δ-phase and γ-phase into spherical shape; or the like. Further, the surface condition is poor when the grains are coarsened. However, if the grains are refined as described above, the above-mentioned heat treatment becomes unnecessary since the segregation of Sn is minimized to a microstructural level. Thus, the surface condition becomes good. In addition, the δ and γ-phases are present in the grain boundary when precipitated. The length of the phases becomes shorter as the grains are dispersed finer and more uniformly; therefore, a specific process for dividing the δ and γ-phases is not required, or set to be minimized when it is required. As described above, the number of required processes can be limited considerably, and thus the manufacturing cost can be reduced as much as possible. Meanwhile, if the condition (5) is satisfied, excellent copper alloy properties are obtainable without accompanying the following problems; that is, if the size of the δ-phase containing a large amount of Sn, a low-melting point metal, is irregular and lacks uniformity, or the δ-phase is not distributed uniformly, the difference in strength between the α-phase in the matrix and the δ-phase causes cracking and impairs the ductility. Furthermore, since the particles of Pb or Bi originally exist at the border between the α-phase and other phases or at the grain boundary, when the phase is large, cracking during solidification is highly likely to occur when the size of the phases is large.

In addition, the cold workability for the first to sixth copper alloy castings is improved as the δ-phase, γ-phase and the particles of Pb, Bi are dispersed further uniformly, and the length or size of said phases and particles get smaller. Therefore, said castings are preferably used for an application requiring caulking process (for example, a hose nipple is subject to caulking process during the installing work).

Generally, if 5 mass % or more of Sn is added, the corrosion resistance is expected to improve considerably. At the same time, Sn is segregated substantially, and thus cracks, shrinkage cavities, blowholes or microporosities are likely to occur during melt-solidification. When the grains are refined during melt-solidification, the above problems do not occur, and the seawater resistance, erosion corrosion resistance or the like is further improved by the addition of a large amount of Sn. In addition, since Zr and P are added only to refine the grains, the inherent properties of a copper alloy casting are not impaired, and thus the grain refinement arising from the addition of Zr and P makes the copper alloy castings secure the same or better properties compared to those of a copper alloy casting having the same composition except for the grain-refining elements Zr and P. In order to make the mean grain size as small as described above during melt-solidification, the content of Zr or the like needs to be determined to satisfy the conditions (1) to (4), and it is preferable that the content of Sn or the like be determined to satisfy the condition (7) for the first to sixth copper alloy castings, and the condition (6) for the third to sixth copper alloy castings in addition to (7).

In the first to sixth copper alloy castings, scrap materials can be used as raw materials. When such scrap materials are used as raw materials, impurities are inevitably contained, which is admitted in a practical casting production. However, if the scrap material is nickel plating material or the like, and Fe and/or Ni are contained as the inevitable impurities, it is required to restrict the contents of Fe and/or Ni. That is, if the contents of Fe and/or Ni are large, Zr and P, which are effective for the grain refinement, are consumed by Fe and/or Ni, thereby deterring the effect of grain refinement. Therefore, when either Fe or Ni is contained, it is preferable to restrict the contents of Fe and Ni within a range, in which the grain refinement is not deterred. Specifically, when either Fe or Ni is contained, it is preferable that the content of Fe or Ni be restricted to be 0.3 mass % or less (more preferably 0.2 mass % or less, further more preferably 0.1 mass % and optimally 0.05 mass % or less). When both Fe and Ni are contained, it is preferable that the total content of Fe and Ni be restricted to be 0.35 mass % or less (more preferably 0.25 mass % or less, further more preferably 0.13 mass % and optimally 0.08 mass % or less).

Since the first to sixth copper alloy castings (particularly, the third to sixth copper alloy castings) have extremely excellent machinability, strength, wear resistance (including the slidability) and corrosion resistance due to the grain refinement and the uniform dispersion of Pb particles or the like, the first to sixth copper alloy castings are used preferably as water contact metal fittings (for example, water faucet of a water supply pipe, metal fitting for water supply and discharge, valves, joints, stem, boiler parts, or the like) used continuously or temporarily in contact with water, friction engaging member (for example, bearing, gear, cylinder, bearing or the like) which makes a relative movement to a facing member (rotating shaft or the like) continuously or temporarily in contact with the facing member or the like, or the structural material thereof.

In addition, the invention proposes a method of casting the first to sixth copper alloy castings with excellent machinability, strength, wear resistance and corrosion resistance, in which Zr (contained to refine the grains further and stably) is added in the form of a copper alloy containing Zr right before pouring or at the final stage of raw material melting, and thus Zr is not added in the form of oxide and/or sulfide during casting. Cu—Zr alloy, Cu—Zn—Zr alloy or an alloy containing one or more elements selected from P, Mg, Al, Sn, Mn and B in addition to the Cu—Zr or Cu—Zn—Zr alloys (base material alloys) is preferable for the copper alloy containing Zr.

That is, in the casting process of the first to sixth copper alloy castings, the losing amount of Zr when added is minimized as possible by adding Zr in the form of an intermediate copper alloy of granular, thin plate, rod, or wire right before pouring. This way, Zr is prevented from being added in the form of oxide and/or sulfide during casting, otherwise it is impossible to secure the amount of Zr required and sufficient for the grain refinement. In addition, when Zr is added right before pouring as described above, since the melting point of Zr is 800 to 1000° C. higher than that of the copper alloy, it is preferable to use the granular (grain diameter: about 2 to 50 mm), thin-plate like (thickness: about 1 to 10 mm), rod-like (diameter: about 2 to 50 mm) or wire-like intermediate alloy in the form of a low melting point alloy having the melting point close to the melting point of the copper alloy and containing a lot of necessary components (for example, Cu—Zn alloy or Cu—Zn—Zr alloy containing 0.5 to 65 mass % of Zr, or an alloy containing one or more element selected from P, Mg, Al, Sn, Mn and B (the content of each element: 0.1 to 5 mass %) added to Cu—Zn or Cu—Zn—Zr, which is a base material alloy). Particularly, in order to decrease the melting point so as to facilitate melting and prevent the loss of Zr, it is preferable to use the intermediate alloy in the form of a Cu—Zn—Zr alloy containing 0.5 to 35 mass % of Zr and 15 to 50 mass % of Zn (preferably a Cu—Zn—Zr alloy containing 1 to 15 mass % of Zr and 25 to 45 mass % of Zn). Although depending on the mixing ratio of Zr to P, Zr impairs the electrical conductivity and thermal conductivity, which are the inherent properties of a copper alloy. However, if the amount of Zr, not in the form of oxide nor sulfide, is 0.045 mass % or less (particularly 0.024 mass % or less), such reduction of electrical and/or thermal conductivity rarely happens, and, even if happens, the reduction is very small compared with the alloy containing no Zr Furthermore, in order to obtain the first to sixth copper alloy castings satisfying the condition (5), it is desirable to properly define the casting conditions, particularly, pouring temperature and cooling rate. That is, with respect to the pouring temperature, it is preferable to determine the temperature to be 20 to 250° c. (more preferably 25 to 150° C.) higher than the liquidus temperature of the copper alloy. That is, it is preferable that (liquidus temperature+20° C.)≤pouring temperature≤(liquidus temperature+250° C.), and it is more preferable that (liquidus temperature+25° C.)≤pouring temperature≤(liquidus temperature+150° C.). Generally, the pouring temperature is 1250° C. or less, preferably 1200° C. or less, and more preferably 1150° C. or less. Even though there is no limitation on the minimum pouring temperature as long as the molten alloy can reach every corner of a mold, the grains tend to be more refined as the pouring temperature is lowered. Meanwhile, it is understood that the temperature conditions vary with the mixing amount of the alloying elements.

The copper alloy castings according to the invention are resistant to the shrinkage during solidification since the grains are refined during melt-solidification, and the generation of defects such as crack or the like can be prevented as much as possible. In addition, in terms of holes or porosity generated during solidification, robust castings including no casting defect or the like are obtainable since gas can be easily escaped. That is, the surface is smooth and shrinkage cavity becomes as shallow as possible since no defect such as porosity or the like is included and dendrite arm is not formed.

The dendrite structure of the copper alloy castings according to the invention, which is crystallized during solidification, is not a typical tree-like casting structure, but has divided arms, preferably in the form of circular, oval, polygonal or cross-like shape. As a result, the flowability of the molten alloy improves, and the molten alloy reaches every corner of a mold even when the mold is thin-walled and complexly shaped.

Since the machinability, strength, wear resistance (slidability) and corrosion resistance of the copper alloy castings of the invention, arising from the alloying elements, are improved by the grain refinement and the uniform dispersion of the phases other than α-phase (that is, including the δ and γ-phases generated by Sn), the segregated Sn or the like, and the particles of Pb or the like, the copper alloy castings of the invention are preferably used as water contact metal fittings (for example, water faucet of a water supply pipe, valves, cocks, joints, flanges, in-house built device, equipments for sewerage, joint clip, boiler parts, or the like) used continuously or temporarily in contact with water (water from a water faucet or the like), friction engaging member (for example, bearing, gear, cylinder, bearing retainer, impeller, pump parts, bearing or the like) making a relative movement to a facing member (rotating shaft or the like) continuously or temporarily in contact with the facing member or the like, or the structural material thereof.

Still furthermore, according to a method of the invention, since the disadvantages caused by the addition of Zr in a form of oxide and/or sulfide do not occur, and the grains are refined by the co-addition of Zr and P, thus the copper alloy castings are cast efficiently and satisfactorily.

BRIEF DESCRIPTION OF THE DRAWINGS

FIG. 1 includes photos of etched surfaces (cross-sectional surfaces) of an embodiment No. 18, in which FIG. 1A shows a macrostructure, and FIG. 1B shows a microstructure.

FIG. 2 includes photos of etched surfaces (cross-sectional surfaces) of a comparative example No. 102, in which FIG. 2A shows a macrostructure, and FIG. 2(B) shows a microstructure.

FIG. 3 includes X-ray micro-analyzer photos of the etched surface (cross-sectional surface) of the embodiment No. 18, in which FIG. 3A shows a composition image; FIG. 3B shows the distribution of Sn; and FIG. 3C shows the distribution of Pb.

FIG. 4 includes X-ray micro-analyzer photos of the etched surface (cross-sectional surface) of the comparative example No. 102, in which FIG. 4A shows a composition image; FIG. 4B shows the distribution of Sn; and FIG. 4C shows the distribution of Pb.

FIG. 5 includes cross sectional views showing a result of the Tatur shrinkage test, in which FIG. 5A shows 'good' test result; FIG. 5B shows 'fair' test result; and FIG. 5C shows 'poor' test result.

FIG. 7 includes front views showing test pieces cast in the casting crack test, in which FIG. 7A shows a test piece with no crack; FIG. 7B shows a test piece with minute cracks; and FIG. 7C shows a test piece with noticeable cracks.

BEST MODE FOR CARRYING OUT THE INVENTION

Embodiment

Figure 3:
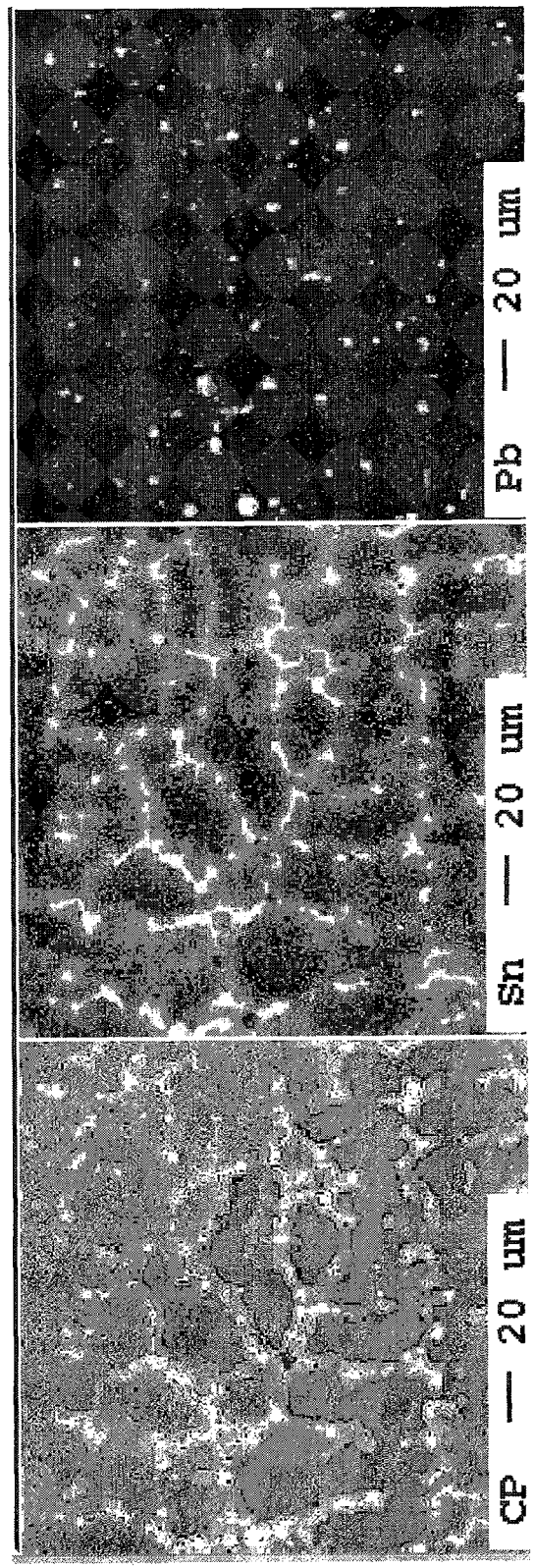

As embodiments, the alloying materials listed in Tables 1 to 3 are melted in an electric furnace, and then each molten alloy obtained is poured into an iron-made mold preheated up to 200° C. so as to cast cylindrical (diameter: 40 mm, and length: 280 mm) castings (hereinafter referred to as 'embodiments') Nos. 1 to 75. In this case, Zr is added to the molten alloy in a granular form of Cu—Zr alloy (a cubic body having several mm long sides) for the embodiments Nos. 1 to 7 corresponding to the first and second copper alloy castings and in a granular form of Cu—Zn—Zr alloy (a cubic body having several mm long sides) for the embodiments Nos. 8 to 75 corresponding to the third to sixth copper alloy castings right before pouring in order to prevent Zr from being added in the form of oxide and/or sulfide. In addition, the pouring temperature is set at 100° C. above the liquidus line temperatures of each copper alloy.

In addition, as comparative examples, the alloying materials listed in Table 4 are melted in an electric furnace, and then the molten alloy is poured into an iron-made mold preheated up to 200° C. under the same conditions as those of the embodiments so as to cast cylindrical (diameter: 40 mm, length: 280 mm) castings (hereinafter referred to as 'comparative examples') Nos. 101 to 117.

A No. 10 specimen pursuant to JIS Z 2201 is taken from each embodiment and each comparative example, and then tensile strength test is performed on the specimen by an AMSLER universal testing machine in order to measure the tensile strength (N/mm$^2$), 0.2% proof stress (N/mm$^2$), elongation (%), and fatigue strength (N/mm$^2$). The results are illustrated in Tables 5 to 8.

In order to verify the wear resistance (slidability) of the embodiments and the comparative examples, the following wear test is performed.

First of all, a ring specimen having the outer diameter of 32 mm and the thickness (axial direction length) of 10 mm is obtained from each embodiment and each comparative example by cutting, drilling or the like. Next, the ring specimen is fit with a rotating shaft and then rotated with a load of 10 kg applied to the ring specimen by making a SUS304-made roll (outer diameter 48 mm) in contact with the outer circumferential surface of the ring specimen. After that, the rotating shaft is rotated at a speed of 209 r.p.m. while multipurpose oil is being dropped on the outer circumferential surface of the specimen. When the specimen rotates hundred thousand times, the rotation of the specimen is stopped, and the mass difference before and after the rotation, that is, wear loss (mg) is measured. It is said that the copper alloy shows more excellent wear resistance as wear loss is smaller, and the results are shown in Tables 5 to 8.

In order to verify the corrosion resistance of the embodiments and the comparative examples, the following erosion corrosion tests I to IV and the dezincification corrosion test designated as 'ISO 6509' are performed.

For the erosion corrosion tests I to IV, a test liquid (30° C.) is sprayed to a specimen taken from the castings through a 1.9 mm diameter nozzle at a speed of 11 m/sec in a perpendicular direction to the axes of the specimen. After a given time has passed, the mass loss (mg/cm$^2$) is measured. As the test liquid, 3% saline solution is used for test I, a mixed saline solution of 3% saline solution and $CuCl_2.2H_2O$ (0.13 g/L) for test II, a mixed liquid of Sodium Hypochlorite Ingestion (NaClO) with a small addition of hydrochloric acid (HCl) for test III, and a 3% saline solution containing glass beads of 0.115 mm in average diameter (5 vol %) for test IV. The mass loss is the mass difference per one square centimeter (mg/cm$^2$) between the mass of the original specimen (before the test) and that of the specimen after being sprayed at with the test liquid for T hours. The spraying time T is 96 hours for test I to III, and 24 hours for test IV. The results of the erosion corrosion test are illustrated in Tables 5 to 8.

For the dezincification corrosion test of 'ISO 6509', a specimen taken from each embodiment and each comparative example is embedded in a phenolic resin material so that the exposed surface of the specimen is perpendicular to the expanding direction of the specimen; and then the surfaces is polished with Emery paper up to No. 1200. After that, the surface is ultrasonic-cleaned in pure water and then dried. The corrosion test specimen thus prepared is soaked in an aqueous solution of 1.0% Cupric Chloride Dihydrate ($CuCl_2.2H_2O$) for 24 hours at a temperature of 75° C., and then the specimen is taken out of the aqueous solution. After that, the maximum depth of dezincification corrosion, that is, the maximum dezincification corrosion depth (μm) is measured. The results are illustrated in Tables 5 to 8.

In addition, in order to verify the machinability of the embodiments and the comparative examples, the following cutting test is performed, and the main cutting force (N) is measured.

That is, a casting of the invention is cut on the outer circumferential surface under the dry condition by a lathe having a point nose straight tool (rake angle: −6°, and nose R: 0.4 mm) at a cutting speed of 100 m/minute, a cutting depth of 1.5 mm, and a feed rate of 0.11 mm/rev. The cutting force is measured by three component dynamometers attached to the bite and then calculated into the main cutting force. The results are shown in Tables 5 to 8.

Figure 8:
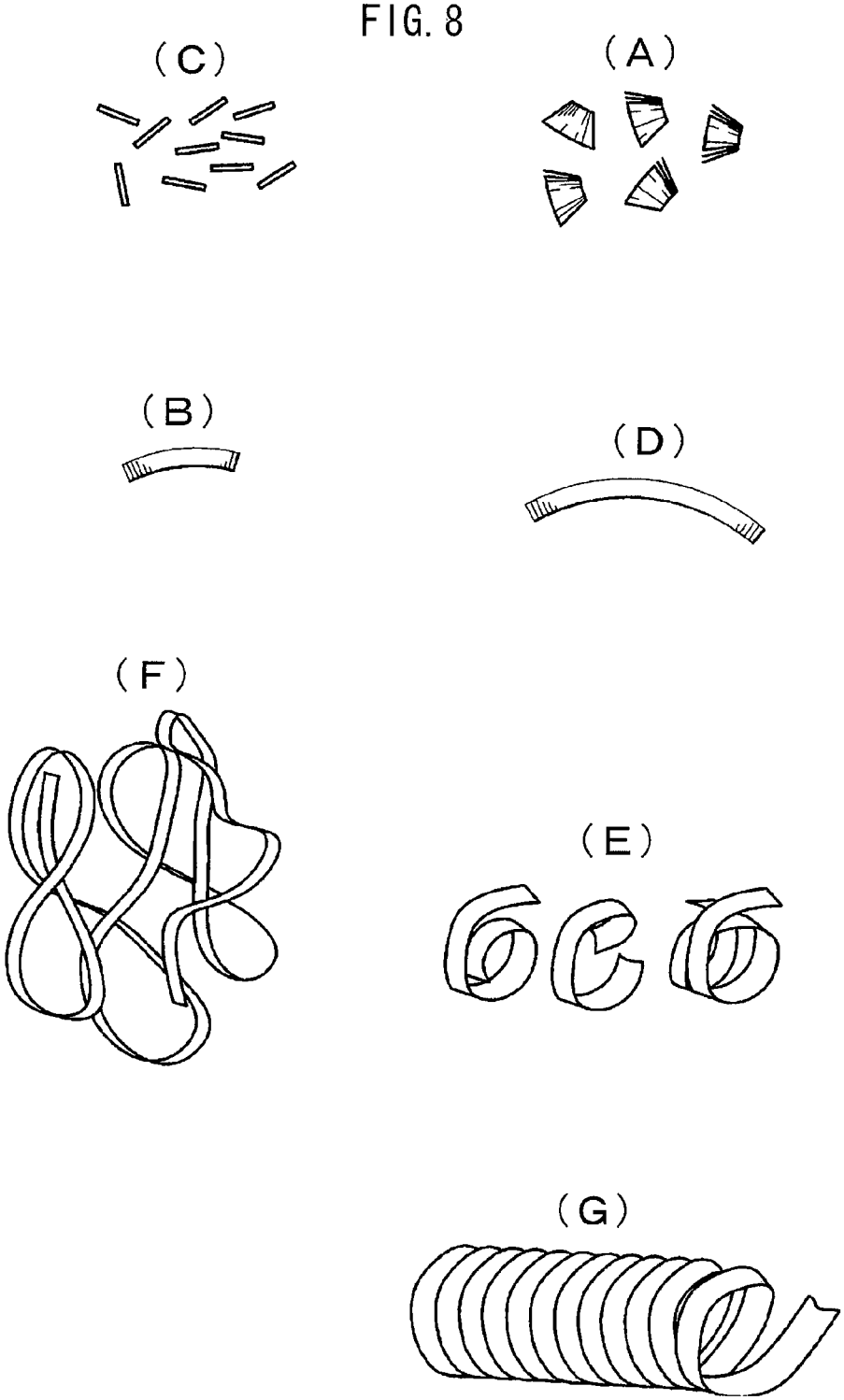
FIG. 8 includes perspective views showing the forms of chips generated during the machining test.

Furthermore, the state of chips generated in the above cutting test is observed, and the machinability of the copper alloy castings is judged by classifying the chips into seven categories on the basis of the shapes of the chips: (a) trapezoidal or triangular small segment shape (FIG. 8A), (b) tape shape having a length of 25 mm or less (FIG. 8B), (c) acicular shape (FIG. 8C), (d) tape shape as long as 75 mm or less (excluding (b)) (FIG. 8D), (e) spiral shape having three or less windings (rolls) (FIG. 8E), (f) tape shape longer than 75 mm (FIG. 8F), and (g) spiral shape having more than three windings (FIG. 8G). The results were shown in Tables 6 and 8. That is, when the chips have the shapes of (f) and (g), the chips are hard to handle (recovery, recycling or the like), and also cause the following troubles: the chips get tangled with the bite of a cutting tool; cut surfaces are damaged; or the like. As a result, satisfactory cutting work cannot be performed. In addition, when the chips have the shapes of (d) and (e), even though they do not cause such serious troubles as the chips of (f) and (g), the chips of (d) and (e) are still hard to handle; They are likely to get tangled with the bite or cut surfaces are likely to be damaged when a continuous cutting process is performed. On the other hand, when the chips have the shapes of (a) to (c), the troubles as described above are not induced, and the chips can be easily handled since they are not as bulky as the chips of (f) and (g). However, in case the chips have the shape of (c), the chips are likely to creep in on the sliding table of a machine tool such as a lathe or the like under a certain working condition and cause mechanical problems, or the chips can be hazardous as they stick the operator in the eye or the finger. Therefore, in the determination of machinability, the shapes of (a) and (b) (particularly, (a)) are graded as the best; the shape of (c) is graded as second best; the shapes of (d) and (e) are graded as industrially acceptable; and the shapes of (f) and (g) are graded as inappropriate.

From the above test results, it is verified that the embodiments are superior in the machinability, mechanical properties (strength, elongation or the like), wear resistance and corrosion resistance to the comparative examples. In addition, although it is commonly considered that elongation is lowered by grain refinement, the result of the tensile strength test shows that the elongation of the copper alloy castings of the invention does not decrease by the grain refinement, but rather improves.

In addition, in order to evaluate the cold workability of the embodiments and the comparative examples, the following cold compression test is performed.

That is, a cylindrical specimen of 5 mm in diameter and 7.5 mm in length is obtained by machining with a lathe from each embodiment and each comparative example, and then compressed by the AMSLER universal test machine. After that, the cold workability is evaluated on the basis of the relation between the existence of cracks and the compression rate (processing rate). The results are illustrated in Tables 6 and 8. In the tables, specimens having cracks at the compression rate of 35% are denoted as 'x' to indicate poor cold workability; specimens having no crack at the compression rate of 50% are denoted as 'O' to indicate good cold workability; and specimens having no crack at the compression rate of 35%, but having cracks at the compression rate of 50% are denoted as 'Δ' to indicate fair cold workability. The cold compression workability can be appreciated as caulking workability, and castings denoted as 'O' are caulked easily and precisely; castings denoted as 'Δ' are caulked at mid-level; and castings denoted as 'x' cannot be caulked properly. It is verified that all embodiments, on which the cold compression workability test is performed, are evaluated 'Δ' or 'O', that is, they have excellent cold workability or caulking workability.

Furthermore, the metal structures (phase structure) after melt-solidification of each embodiment and each comparative example at the room temperature is verified, and the area ratios (%) of α, γ and δ-phases are measured by image analysis. That is, the structures of the casting, magnified 200 times by an optical microscope, is expressed in the binary system with an image processing software 'WinROOF', and then the area ratio of each phase is measured. The area ratio is measured in three different fields, and the average value of the three area ratios is regarded as the phase ratio of each phase. The results of the metal structures are illustrated in Tables 1 to 4, and all the embodiments satisfy the condition (4). In addition, in all embodiments, the primary crystals during melt-solidification in casting process are α-phase, thereby satisfying the condition (8).

Still furthermore, the mean grain sizes (μm) of each embodiment and each comparative example during melt-solidification is measured. That is, a casting is cut, and the cross-sectional surface is etched by nitric acid. After that, the mean grain size of the microstructure displayed on the etched surface is measured. The measurement is based on the comparative method for estimating average grain size of wrought copper and copper alloys according to JIS H0501, in which grains having the diameter of more than 0.5 mm are observed by naked eyes, and grains having the diameter of 0.5 mm or less are magnified 7.5 times and then observed after the cut surface is etched by nitric acid. In addition, grains having the diameter of less than about 0.1 mm are etched by a mixed liquid of hydrogen peroxide and ammonia water and then magnified 75 times by an optical microscope for observation. The results are illustrated in Tables 5 to 8, and all the embodiments satisfy the condition (5). Meanwhile, in the comparative example No. 117 containing a proper amount of Zr but no content of P, the grains are refined only slightly. From this standpoint, it is understood that the single addition of Zr is not sufficient to work on grain refinement, and it is required to add Zr and P together to refine the grains significantly. Furthermore, it is verified that the embodiments also satisfy the conditions (10) to (13). FIGS. 1 to 4 are displayed as an example.

FIG. 1 includes a photo of the macrostructure (FIG. 1A) and a photo of the microstructure (FIG. 1B) of the embodiment No. 18, and FIG. 2 includes a photo of the macrostructure (FIG. 2A) and a photo of the microstructure (FIG. 2B) of the comparative example No. 102. It is evident from FIGS. 1 and 2 that the comparative example No. 102 does not satisfy the conditions (10) and (11) whereas the embodiment No. 18 satisfies the conditions (10) and (11).

Figure 4:
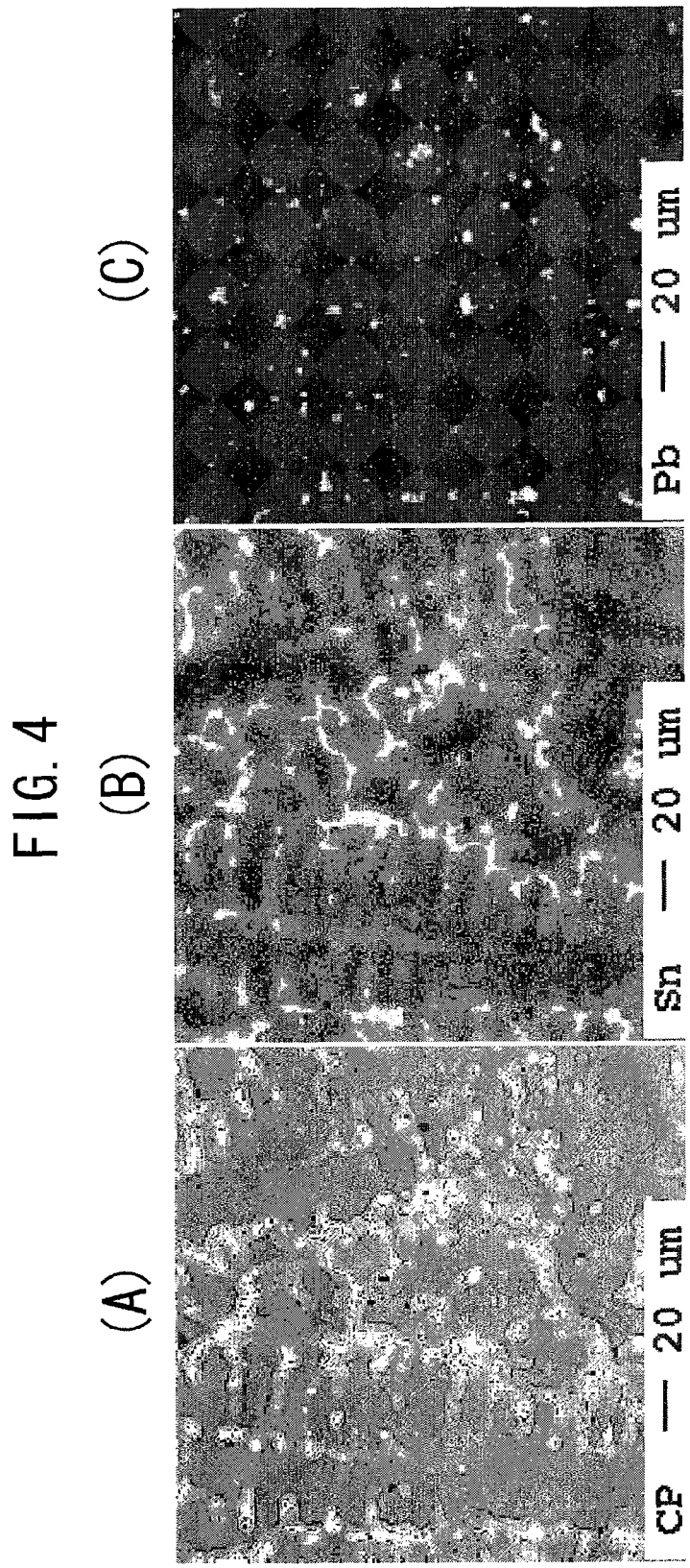

FIG. 3 includes X-ray micro-analyzer photos of the embodiment No. 18, in which FIG. 3A shows a composition image; FIG. 3B shows the distribution of Sn; and FIG. 3C shows the distribution of Pb. FIG. 4 includes X-ray micro-analyzer photos of the comparative example No. 102, in which FIG. 4A shows a composition image; FIG. 4B shows the distribution of Sn; and FIG. 4C shows the distribution of Pb. It is evident from FIG. 3 that, in the embodiment No. 18, the high Sn-concentrated areas (white areas in FIG. 3B) and the Pb particles (white areas in FIG. 3C) are small and uniform in size, and are distributed evenly, thereby satisfying the conditions (12) and (13). On the other hand, in the comparative example No. 102, as shown in FIG. 4, the high Sn-concentrated areas (white areas in FIG. 4B) and the Pb particles (white areas in FIG. 4C) are not uniform in size and are distributed unevenly, thereby not satisfying the conditions (12) and (13).

In addition, the comparative example No. 102 has almost the same composition as that of the embodiment No. 18 except that the content of Zr does not reach the lower limit of the above-described proper range. From this point of view, it is understood that, when a proper amount of Zr and P is added together under the above-described conditions, the grains are refined effectively, and the particles of Pb or the like are made smaller and dispersed. Furthermore, according to the results of the wear test (wear loss) and the cutting test, it is evident that the embodiment No. 18 has more excellent wear resistance and machinability than the comparative example No. 102. Therefore, it can be understood that satisfying the conditions (11) to (14) is an important factor in further improving the wear resistance (slidability) and machinability.

From the above facts, it is verified that, when an embodiment contains the components in the above-described ranges and satisfies the conditions (1) to (5) (or the conditions (1) to (6) in the case of the third to sixth copper alloy castings), the embodiment has much more improved machinability, strength, wear resistance and corrosion resistance than the comparative example not satisfying any of the above conditions. In addition, it is also verified that the improved properties as described above can be achieved more effectively if the conditions (7) to (13) are satisfied in addition to the above conditions.

It is also considered that the castability can be improved by satisfying the condition (5), that is, by refining the grains. In order to verify this, the following Tatur shrinkage test and casting-cracking test are performed.

Figure 5:
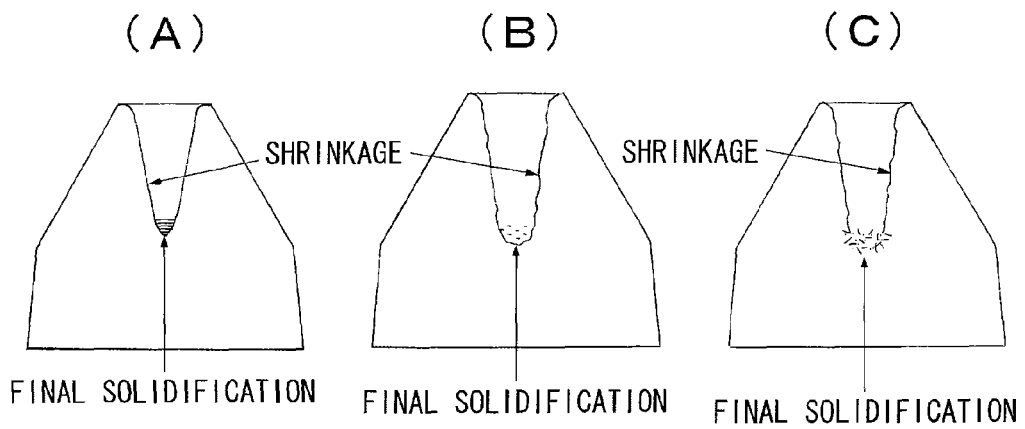

That is, Tatur shrinkage test is conducted on the molten alloys (of the copper alloy materials having the compositions listed in Tables 1 to 4) used in casting the embodiments and the comparative examples. Then the castability is evaluated by examining the shapes of internal shrinkage area and the existence of casting defects such as porosity, hole, shrinkage cavity or the like in the vicinity of the internal shrinkage area. The castability is evaluated as 'good' for a casting having a smooth internal shrinkage area and no defect such as porosity or the like in the final solidification area as shown in FIG. 5A; 'poor' for a casting having a remarkably uneven internal shrinkage area and defects such as porosity or the like in the final solidification area as shown in FIG. 5C, and 'slightly poor' for a casting evaluated neither 'good' nor 'poor' as shown in FIG. 5B. The results are illustrated in Tables 5 to 8. In the tables, 'good' is denoted as 'O'; 'slightly poor' is denoted as 'Δ'; and 'poor' is denoted as 'x'. In addition, the grain size in the macrostructure is checked for each casting obtained by the Tatur shrinkage test. The results are illustrated in Tables 5 to 8. In the tables, castings having the grain size of 100 μm or less are denoted as 'O'; castings having the grain size in the range of 100 to 300 μm are denoted as 'Δ'; and castings having the grain size of more than 300 μm are denoted as 'x'. The results correspond to the results of the mean grain size measured for the embodiments and the comparative examples as described above.

From Tables 5 to 8, which show the results of the Tatur Shrinkage Test, a very few embodiments are graded as 'slightly bad' while the majority is graded as 'good', and it is verified that the embodiments have much more excellent castability due to the grain refinement than the comparative examples, most of which are graded as 'poor'.

Figure 6:
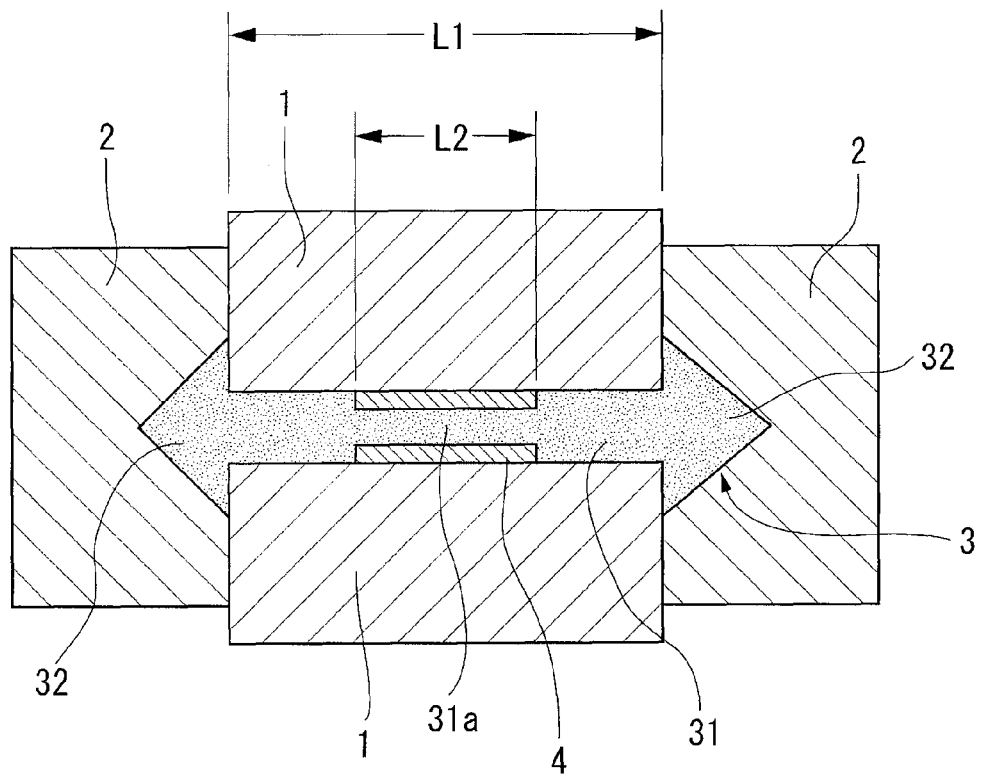
FIG. 6 is a front view of a vertically cross-sectioned test piece showing the casting state in a casting crack test.

Still furthermore, in the casting crack test, as shown in FIG. 6, a test piece 3 is cast by using the top mold 1 and the bottom mold 1, and the right mold 2 and the left mold 2. Then the castability is examined by the fact whether cracks occur in the test piece 3. That is, the test piece 3 is cast in a shape of a two-headed arrow consisting of a band plate 31 in the midsection with two triangular plates 32 and 32 affixed to the each end of the band plate. The central part of the band plate 31 is considered as crack judgment area 31a (castability is measured by the cracks occurred in this area). The band plate 31 is cast in the cavity between the top and bottom molds (1 and 1). Inside the molds are partly placed heat insulation material 4 so that the crack judgment area 31a is cast in this particular area of the cavity surrounded by the heat insulation material 4 (where solidification slows down). There are two other cavities formed by the right and left molds (2 and 2) where the triangular plate 32 is cast in each mold. When a molten alloy is poured into the cavities, the solidification in the crack judgment area 31a proceeds slower than the other areas due to the heat insulation material 4. When the band plate 31 shrinks in the longitudinal direction by solidification, the triangular plates 32 and 32 restrict the shrinkage. Therefore, the stress arising from the shrinkage is centralized in the crack judgment area 31a where the molten alloy is solidified slower. As such, castability is evaluated by the presence of cracks in the crack judgment area 31a. In the casting crack test, L1, the length of the band plate 31, and L2, the length of the crack judgment area 31a are set to be 200 mm and 100 mm, respectively. As conducted in the Tatur Shrinkage Test, the test piece 3 is cast with a molten alloy used when the embodiments and the comparative examples are cast (molten alloy of a copper alloy having the compositions illustrated in Tables 1 to 4). The results are illustrated in Tables 5 to 8. In the castability evaluation, as shown in FIG. 7C, when a noticeable crack 33a in the crack judgment area 31a is visually examined in a test piece casting, the casting is evaluated to have poor castability, thereby being denoted as 'x' In addition, as shown in FIG. 7A, when no crack is observed in the crack judgment area 31a with naked eye or even with five-time magnification glass, the casting is evaluated to have excellent castability, thereby being denoted as 'O'. Furthermore, as shown in FIG. 7B, when a test piece casting, in which no noticeable crack 33a can be found in the crack judgment area 31a by a visual examination, has a minor crack 33b observed with five-time magnification glass is evaluated to have normal castability, thereby being denoted as 'Δ'. It is verified from the casting crack test that the castings according to the invention have excellent castability since almost all of the embodiments are graded as 'O' with extremely small number of embodiments graded as 'Δ'.

Meanwhile, if the solid phase is granulated in a semi-solid metal state, naturally, the semi-solid metal castability becomes excellent, and thus the satisfactory semi-solid metal casting can be performed. The flowability of a molten liquid containing solid phases at the final stage of solidification depends mainly on the shape of the solid phase, and the viscosity and composition of the liquid phase in a semi-solid metal state. Specifically, the casting moldability (a property determining whether or not a robust casting is obtainable even when a precision casting or a casting of a complicated shape is required) is more influenced by the former factor, that is, the shape of the solid phase. If the solid phase begins to form a network of dendrite in a semi-solid metal state, the casting moldability deteriorates since the molten liquid containing such solid phase is hard to fill in every corner of a mold. Therefore, a precision casting or a casting of a complicated shape is difficult to be realized. Meanwhile, when the solid phase is granulated in a semi-solid metal state, and when the shape of the solid phase becomes more spherical (more circular in two-dimension) and smaller, castability including the semi-solid metal castability becomes more excellent. As a result, a robust precision casting or a casting of complicated shape can be obtainable. (Naturally, high-quality semi-solid metal castings are realized). Therefore, the semi-solid metal castability can be evaluated by examining the shape of the solid phase in a semi-solid metal state. Also, other castability including complicated shape castability, precision castability and semi-solid metal forgeability can be evaluated by the semi-solid metal castability. Generally, the semi-solid metal castability is graded as good when, in a semi-solid metal state including 30 to 80% of solid phase, the dendrite network is divided in the crystal structure and the two-dimensional shape of the solid phase is circular, substantially circular, oval, cross-like or polygonal; and further, in a semi-solid metal state including 60% of solid phase particularly, the semi-solid metal castability is graded as excellent either when the mean grain size of the solid phase is 150 μm or less (preferably 100 μm or less, and more preferably 50 μm or less) or when the average maximum length of the solid phase is 300 μm or less (preferably 150 μm or less, and more preferably 100 μm or less).

In order to evaluate the semi-solid metal castability of the embodiments and the comparative examples, the following semi-solid metal castability test is performed.

In the semi-solid metal castability test, the raw materials used in casting the embodiments and the comparative examples are charged into a crucible; heated up to the temperature where the raw materials come into the semi-solid metal state (solid phase ratio: about 60%). Then the semi-solid metal molten thus obtained is held at the above temperature for 5 minutes and then quenched rapidly (by water cooling). After that, the shape of the solid phase in the semi-solid metal state is investigated so as to evaluate the semi-solid metal castability. The results are illustrated in Tables 5 and 8. It is verified that each embodiment shows excellent semi-solid metal castability. Meanwhile, in the tables, a casting having the mean grain size of 150 μm or less or the mean maximum grain length of 300 μm or less is denoted as 'O' to indicate excellent semi-solid metal castability; a casting having the grain size not satisfying the above condition, but having no dendrite network therein is denoted as 'Δ' to indicate industrially satisfactory semi-solid metal castability; and a casting having dendrite network therein is denoted as 'x' to indicate poor semi-solid metal castability.

Furthermore, a new casting (hereinafter referred to as 'recycled casting') is cast by using the copper alloy casting No. 11 (hereinafter referred to as 'casting product') as a raw material, which was obtained as an embodiment. That is, the casting product (the copper alloy casting No. 11) is re-melted at the temperature of 1100° C. under a charcoal coating and held for 5 minutes, and then Cu—Zn—Zr alloy containing 3 mass % of Zr is further added to the molten alloy to compensate for the Zr loss caused by oxidation while melting, based on the assumption that the Zr loss would be 0.003 mass %. After that, the molten alloy made from the casting product is poured into a mold. The recycled casting thus obtained contains almost the same amount of Zr (0.019 mass %) as that of the casting product No. 11 used as the raw material. The mean grain size of the recycled casting is also almost equal to that of the casting product No. 11, that is, 40 µm. From these points, it is verified that, for the copper alloy casting of the invention, the surplus or unnecessary parts such as runner or the like, which are generated during the casting process, are effectively reused as a recycling material without impairing the effect of grain refinement. Therefore, such surplus or unnecessary parts such as runner or the like can be charged as a replenishing material during a continuous operation, which makes the continuous operation extremely efficient and effective costwise as well.

TABLE 1

| Casting No. | | Alloy Composition (mass %) | | | | | | | | | | | | | | $\alpha + \gamma + \delta$ Total Area Ratio (%) |
|---|---|---|---|---|---|---|---|---|---|---|---|---|---|---|---|---|
| | | Cu | Zn | Zr | P | Sn | Pb | Bi | Mn | Al | Mg | f1 | f2 | f3 | f4 | f5 | |
| EMBODIMENT | 1 | 80.1 | | 0.02 | 0.08 | 6.8 | 13 | | | | | 4.0 | 1020 | 255 | 20.4 | 83.0 | 100 |
| | 2 | 88.9 | | 0.03 | 0.07 | 4.3 | 6.7 | | | | | 2.3 | 430 | 184 | 12.9 | 89.9 | 100 |
| | 3 | 80.4 | | 0.03 | 0.07 | 10 | 9.5 | | | | | 2.3 | 1000 | 429 | 30.0 | 79.9 | 100 |
| | 4 | 80.4 | | 0.02 | 0.08 | 6.5 | | 13 | | | | 4.0 | 975 | 244 | 19.5 | 83.4 | 100 |
| | 5 | 90 | | 0.03 | 0.07 | 4.8 | | 5 | | | | 2.3 | 480 | 206 | 14.4 | 89.9 | 100 |
| | 6 | 86.3 | | 0.03 | 0.14 | 6.5 | 7 | | | 0.03 | | 4.7 | 650 | 139 | 19.5 | 86.1 | 100 |
| | 7 | 87.9 | | 0.03 | 0.09 | 3.9 | | 8 | 0.07 | | 0.01 | 3.0 | 390 | 130 | 11.7 | 89.7 | 100 |
| | 8 | 73.6 | 16.45 | 0.016 | 0.03 | 5.2 | 4.7 | | | | | 1.9 | 2003 | 1068 | 32.1 | 73.3 | 100 |
| | 9 | 76.1 | 14.15 | 0.015 | 0.04 | 5.1 | 4.6 | | | | | 2.7 | 1963 | 736 | 29.4 | 75.7 | 100 |
| | 10 | 78.4 | 11.70 | 0.014 | 0.09 | 5 | 4.8 | | | | | 6.4 | 1907 | 297 | 26.7 | 78.0 | 100 |
| | 11 | 79.4 | 10.87 | 0.019 | 0.11 | 5 | 4.6 | | | | | 5.8 | 1362 | 235 | 25.9 | 78.9 | 100 |
| | 12 | 81.6 | 8.30 | 0.025 | 0.08 | 5.1 | 4.9 | | | | | 3.2 | 944 | 295 | 23.6 | 81.3 | 100 |
| | 13 | 84.2 | 5.60 | 0.026 | 0.07 | 5.2 | 4.9 | | | | | 2.7 | 816 | 303 | 21.2 | 83.8 | 100 |
| | 14 | 85.6 | 4.48 | 0.019 | 0.1 | 5.1 | 4.7 | | | | | 5.3 | 1041 | 198 | 19.8 | 85.1 | 100 |
| | 15 | 80.3 | 9.65 | 0.0029 | 0.05 | 5.2 | 4.8 | | | | | 17.2 | 8706 | 505 | 25.2 | 80.0 | 100 |
| | 16 | 80.4 | 9.60 | 0.0062 | 0.09 | 5.3 | 4.6 | | | | | 14.5 | 4114 | 283 | 25.5 | 79.8 | 100 |
| | 17 | 80 | 9.99 | 0.0089 | 0.1 | 5.1 | 4.8 | | | | | 11.2 | 2842 | 253 | 25.3 | 79.6 | 100 |
| | 18 | 80.3 | 9.88 | 0.019 | 0.1 | 5 | 4.7 | | | | | 5.3 | 1310 | 249 | 24.9 | 79.9 | 100 |
| | 19 | 80.4 | 9.78 | 0.027 | 0.09 | 5 | 4.7 | | | | | 3.3 | 918 | 275 | 24.8 | 80.0 | 100 |
| | 20 | 80 | 9.95 | 0.038 | 0.11 | 5.1 | 4.8 | | | | | 2.9 | 665 | 230 | 25.3 | 79.5 | 100 |
| | 21 | 80.5 | 9.39 | 0.017 | 0.09 | 5.1 | 4.9 | | | | | 5.3 | 1453 | 274 | 24.7 | 80.1 | 100 |
| | 22 | 80 | 10.26 | 0.023 | 0.016 | 5.1 | 4.6 | | | | | 0.7 | 1111 | 1598 | 25.6 | 79.7 | 100 |
| | 23 | 80.5 | 9.56 | 0.019 | 0.024 | 5.2 | 4.7 | | | | | 1.3 | 1324 | 1048 | 25.2 | 80.2 | 100 |
| | 24 | 80.1 | 10.04 | 0.022 | 0.036 | 5.2 | 4.6 | | | | | 1.6 | 1166 | 712 | 25.6 | 79.7 | 100 |
| | 25 | 80.3 | 9.64 | 0.019 | 0.046 | 5.2 | 4.8 | | | | | 2.4 | 1328 | 549 | 25.2 | 80.0 | 100 |
| | 26 | 80.3 | 9.34 | 0.018 | 0.14 | 5.3 | 4.9 | | | | | 7.8 | 1402 | 180 | 25.2 | 79.7 | 100 |

TABLE 2

| Casting No. | | Alloy Composition (mass %) | | | | | | | f1 | f2 | f3 | f4 | f5 | $\alpha + \gamma + \delta$ Total Area Ratio (%) |
|---|---|---|---|---|---|---|---|---|---|---|---|---|---|---|
| | | Cu | Zn | Zr | P | Sn | Pb | Bi | | | | | | |
| EMBODIMENT | 27 | 80.2 | 9.62 | 0.018 | 0.16 | 5.1 | 4.9 | | 8.9 | 1385 | 156 | 24.9 | 79.6 | 100 |
| | 28 | 80.5 | 9.39 | 0.019 | 0.19 | 5.2 | 4.7 | | 10.0 | 1315 | 132 | 25.0 | 79.7 | 100 |
| | 29 | 80.6 | 9.35 | 0.018 | 0.23 | 5 | 4.8 | | 12.8 | 1353 | 106 | 24.4 | 79.8 | 100 |
| | 30 | 80.2 | 9.93 | 0.0046 | 0.17 | 5.1 | 4.6 | | 37.0 | 5484 | 148 | 25.5 | 79.4 | 100 |
| | 31 | 80.4 | 9.84 | 0.035 | 0.022 | 5 | 4.7 | | 0.6 | 710 | 1129 | 24.8 | 80.2 | 100 |
| | 32 | 87.4 | 0.49 | 0.023 | 0.09 | 10.8 | 1.2 | | 3.9 | 1430 | 365 | 32.9 | 82.3 | 100 |
| | 33 | 88.1 | 2.80 | 0.022 | 0.08 | 8.3 | 0.7 | | 3.6 | 1259 | 346 | 27.7 | 84.1 | 100 |
| | 34 | 86.5 | 2.20 | 0.019 | 0.08 | 9.6 | 1.6 | | 4.2 | 1632 | 388 | 31.0 | 82.3 | 100 |
| | 35 | 77.6 | 17.31 | 0.017 | 0.07 | 5.3 | 2.7 | | 4.1 | 1777 | 432 | 30.2 | 76.1 | 100 |
| | 36 | 63.2 | 8.60 | 0.019 | 0.08 | 2.8 | 5.3 | | 4.2 | 895 | 213 | 17.0 | 84.2 | 100 |
| | 37 | 77.5 | 12.59 | 0.016 | 0.09 | 3.4 | 6.4 | | 5.6 | 1425 | 253 | 22.8 | 7.7 | 100 |
| | 38 | 75.4 | 15.83 | 0.017 | 0.05 | 2.5 | 6.2 | | 2.9 | 1373 | 467 | 23.3 | 77.1 | 100 |
| | 39 | 77.8 | 16.03 | 0.015 | 0.06 | 0.6 | 5.5 | | 4.0 | 1189 | 297 | 17.8 | 80.1 | 100 |
| | 40 | 77.5 | 15.61 | 0.009 | 0.08 | 1.6 | 5.2 | | 8.9 | 2268 | 255 | 20.4 | 79.1 | 100 |
| | 41 | 82.5 | 3.37 | 0.016 | 0.11 | 6.9 | 7.1 | | 6.9 | 1505 | 219 | 24.1 | 82.3 | 100 |
| | 42 | 85 | 0.47 | 0.019 | 0.11 | 5.2 | 9.2 | | 5.8 | 846 | 146 | 16.1 | 86.7 | 100 |
| | 43 | 80 | 0.68 | 0.019 | 0.1 | 8 | 11.2 | | 5.3 | 1299 | 247 | 24.7 | 81.3 | 100 |
| | 44 | 80.6 | 13.37 | 0.016 | 0.11 | 5.2 | 0.7 | | 6.9 | 1811 | 263 | 29.0 | 78.0 | 100 |
| | 45 | 81 | 13.40 | 0.015 | 0.09 | 5.2 | 0.3 | | 6.0 | 1933 | 322 | 29.0 | 78.3 | 100 |
| | 46 | 80 | 14.55 | 0.016 | 0.08 | 5.2 | 0.15 | | 5.0 | 1885 | 377 | 30.2 | 77.2 | 100 |
| | 47 | 82.7 | 9.70 | 0.0065 | 0.09 | 5.4 | | 2.1 | 13.8 | 3985 | 288 | 25.9 | 80.8 | 100 |
| | 48 | 82.4 | 10.08 | 0.018 | 0.1 | 5.3 | | 2.1 | 5.6 | 1443 | 260 | 26.0 | 80.5 | 100 |
| | 49 | 82.6 | 9.88 | 0.023 | 0.1 | 5.3 | | 2.1 | 4.3 | 1121 | 258 | 25.8 | 80.7 | 100 |
| | 50 | 82.5 | 9.98 | 0.029 | 0.09 | 5.4 | | 2 | 3.1 | 903 | 291 | 26.2 | 80.5 | 100 |
| | 51 | 77.5 | 15.30 | 0.018 | 0.08 | 5.3 | | 1.8 | 4.4 | 1733 | 390 | 31.2 | 75.5 | 100 |
| | 52 | 77.4 | 16.85 | 0.014 | 0.035 | 2.5 | | 3.2 | 2.5 | 1739 | 696 | 24.4 | 77.6 | 100 |

TABLE 3

| Casting No. | | Alloy Composition (mass %) | | | | | | | | | | |
|---|---|---|---|---|---|---|---|---|---|---|---|---|
| | | Cu | Zn | Zr | P | Sn | Pb | Bi | Se | Te | As | Sb | Mn |
| EMBODIMENT | 53 | 84.5 | 8.38 | 0.019 | 0.1 | 5.4 | | 1.2 | 0.4 | | | | |
| | 54 | 86 | 5.98 | 0.024 | 0.1 | 5.3 | | 1.8 | 0.8 | | | | |
| | 55 | 88.1 | 2.60 | 0.023 | 0.08 | 8.3 | | 0.6 | | 0.3 | | | |
| | 56 | 78.9 | 12.99 | 0.024 | 0.09 | 5.3 | | 2.7 | | | | | |
| | 57 | 80.1 | 0.27 | 0.019 | 0.11 | 10 | | 9.5 | | | | | |
| | 58 | 80 | 14.03 | 0.015 | 0.06 | 5.2 | | 0.7 | | | | | |
| | 59 | 81.8 | 12.05 | 0.018 | 0.08 | 5.1 | | 0.8 | 0.15 | | | | |
| | 60 | 78.5 | 14.11 | 0.016 | 0.07 | 5 | | 2.3 | | | | | |
| | 61 | 77.9 | 13.89 | 0.017 | 0.09 | 5.2 | | 2.3 | 0.6 | | | | |
| | 62 | 77 | 15.34 | 0.009 | 0.05 | 5.1 | | 2.5 | | | | | |
| | 63 | 80.7 | 9.27 | 0.02 | 0.08 | 5.3 | 4.6 | | | | | | |
| | 64 | 80.5 | 9.36 | 0.015 | 0.08 | 5.3 | 4.7 | | | | | | |
| | 65 | 73.8 | 15.95 | 0.014 | 0.09 | 5.2 | 4.9 | | | | 0.05 | | |
| | 66 | 75.4 | 15.78 | 0.009 | 0.04 | 2.5 | 6.2 | | | | 0.02 | 0.05 | |
| | 67 | 84.1 | 5.74 | 0.019 | 0.1 | 5.1 | 4.9 | | | | | 0.04 | |
| | 68 | 80.5 | 12.93 | 0.017 | 0.11 | 5.2 | | 0.9 | 0.3 | | 0.04 | | |
| | 69 | 75.6 | 15.52 | 0.015 | 0.09 | 2.5 | 6.2 | | | | | | 0.08 |
| | 70 | 84 | 5.88 | 0.024 | 0.07 | 5.1 | 4.9 | | | | | | |
| | 71 | 80.5 | 13.04 | 0.018 | 0.13 | 5.2 | | 0.7 | | 0.4 | | | |
| | 72 | 82.4 | 9.97 | 0.024 | 0.1 | 5.4 | | 2.1 | | | | | |
| | 73 | 75.8 | 15.34 | 0.009 | 0.05 | 2.5 | 6.2 | | | | 0.02 | 0.03 | 0.05 |
| | 74 | 80 | 13.23 | 0.019 | 0.11 | 5.2 | | 1 | 0.4 | | | 0.04 | |
| | 75 | 82.3 | 10.01 | 0.022 | 0.1 | 5.4 | | 2.1 | | 0.05 | | | |

| Casting No. | | Alloy Composition (mass %) | | | | | | | | α + γ + δ Total Area Ratio (%) |
|---|---|---|---|---|---|---|---|---|---|---|
| | | Al | Mg | Impurities | | f1 | f2 | f3 | f4 | f5 | |
| EMBODIMENT | 53 | | | Fe | Ni | 5.3 | 1294 | 246 | 24.6 | 82.3 | 100 |
| | 54 | | | | | 4.2 | 912 | 219 | 21.9 | 84.4 | 100 |
| | 55 | | | | | 3.5 | 1196 | 344 | 27.5 | 84.2 | 100 |
| | 56 | | | | | 3.8 | 1204 | 321 | 28.9 | 77.3 | 100 |
| | 57 | | | | | 5.8 | 1593 | 275 | 30.3 | 79.5 | 100 |
| | 58 | | | | | 4.0 | 1975 | 494 | 29.6 | 77.6 | 100 |
| | 59 | | | | | 4.4 | 1520 | 342 | 27.4 | 79.5 | 100 |
| | 60 | | | | | 4.4 | 1820 | 416 | 29.1 | 79.6 | 100 |
| | 61 | | | | | 5.3 | 1735 | 328 | 29.5 | 76.5 | 100 |
| | 62 | | | | | 5.6 | 3405 | 613 | 30.6 | 75.6 | 100 |
| | 63 | | | 0.05 | 0.03 | 4.0 | 1259 | 315 | 25.2 | 80.1 | 100 |
| | 64 | | | 0.03 | 0.008 | 5.3 | 1684 | 316 | 25.3 | 80.0 | 100 |
| | 65 | | | | | 6.4 | 2253 | 351 | 31.5 | 73.4 | 100 |
| | 66 | | | | | 4.4 | 2587 | 582 | 23.3 | 77.1 | 100 |
| | 67 | | | | | 5.3 | 1107 | 210 | 21.0 | 83.7 | 100 |
| | 68 | | | | | 6.5 | 1678 | 259 | 28.5 | 78.2 | 100 |
| | 69 | | | | | 6.0 | 1534 | 256 | 23.0 | 77.2 | 100 |
| | 70 | 0.03 | | | | 2.9 | 882 | 303 | 21.2 | 83.7 | 100 |
| | 71 | | 0.008 | | | 7.2 | 1591 | 220 | 28.6 | 78.1 | 100 |
| | 72 | 0.007 | 0.002 | | | 4.2 | 1090 | 262 | 26.2 | 80.4 | 100 |
| | 73 | | | | | 5.6 | 2538 | 457 | 22.8 | 77.5 | 100 |
| | 74 | | 0.006 | | | 5.8 | 1517 | 262 | 28.8 | 77.7 | 100 |
| | 75 | 0.015 | | | | 4.5 | 1192 | 262 | 26.2 | 80.3 | 100 |

TABLE 4

| Casting No. | | Alloy Composition (mass %) | | | | | | | | | | | | | | | α + γ + δ Total Area Ratio (%) |
|---|---|---|---|---|---|---|---|---|---|---|---|---|---|---|---|---|---|
| | | Cu | Zn | Zr | P | Sn | Pb | Bi | Se | Impurities | | f1 | f2 | f3 | f4 | f5 | |
| COMP. EX. | 101 | 92.3 | 0.89 | 0.016 | 0.09 | 1.8 | 4.9 | | | Fe | Ni | 5.6 | 393 | 70 | 6.3 | 93.6 | 100 |
| | 102 | 80.1 | 9.76 | 0.0008 | 0.04 | 5.2 | 4.9 | | | | | 50.0 | 31699 | 634 | 25.4 | 79.8 | 100 |
| | 103 | 80.3 | 9.84 | 0.08 | 0.08 | 5 | 4.7 | | | | | 1.0 | 311 | 311 | 24.8 | 79.9 | 100 |
| | 104 | 80.4 | 9.66 | 0.028 | 0.012 | 5 | 4.9 | | | | | 0.4 | 881 | 2055 | 24.7 | 80.3 | 100 |
| | 105 | 80.7 | 8.93 | 0.0095 | 0.36 | 5.3 | 4.7 | | | | | 37.9 | 2614 | 69 | 24.8 | 79.3 | 100 |
| | 106 | 87.5 | 0.28 | 0.0007 | 0.12 | 109 | 1.2 | | | | | 171.4 | 47113 | 275 | 33.0 | 82.3 | 100 |
| | 107 | 80.4 | | 0.0006 | 0.07 | 10 | 9.5 | | | | | 116.7 | 50000 | 429 | 30.0 | 79.9 | 100 |
| | 108 | 82.6 | 9.99 | 0.0007 | 0.11 | 5.3 | | 2 | | | | 157.1 | 36985 | 235 | 25.9 | 80.6 | 100 |

TABLE 4-continued

| Casting No. | Alloy Composition (mass %) | | | | | | | | | | | | | | α + γ + δ Total Area Ratio (%) |
|---|---|---|---|---|---|---|---|---|---|---|---|---|---|---|---|
| | Cu | Zn | Zr | P | Sn | Pb | Bi | Se | Impurities | f1 | f2 | f3 | f4 | f5 | |
| 109 | 80 | 0.47 | 0.0004 | 0.028 | 10 | 9.5 | | | | 70.0 | 76179 | 1088 | 30.5 | 79.7 | 100 |
| 110 | 80.2 | 9.64 | 0.018 | 0.08 | 5.2 | 4.6 | | | 0.26 | 4.4 | 1402 | 316 | 25.2 | 79.7 | 100 |
| 111 | 80 | 9.84 | 0.022 | 0.07 | 5.3 | 4.5 | | 0.27 | | 3.2 | 1170 | 368 | 25.7 | 79.4 | 100 |
| 112 | 80.5 | 9.45 | 0.022 | 0.07 | 5.3 | 4.5 | 0.16 | 0.16 | | 3.2 | 1152 | 362 | 25.3 | 79.9 | 100 |
| 113 | 84.3 | 5.87 | 0 | 0.03 | 4.9 | 4.9 | | | | | | | | 84.2 | |
| 114 | 83.6 | 9.06 | 0 | 0.04 | 4.6 | | 2.7 | | | | | | | 82.5 | |
| 115 | 86.4 | 5.86 | 0 | 0.04 | 5.1 | | 1.8 | 0.8 | | | | | | 85.0 | |
| 116 | 61.5 | 35.20 | 0 | 0 | 0.2 | 3.1 | | | | | | | | 63.0 | |
| 117 | 80.5 | 9.67 | 0.035 | | 5 | 4.8 | | | | 0 | 705 | | 24.7 | 80.4 | 100 |

TABLE 5

| Casting No. | Mean Grain Size (μm) | Tatur Shrinkage Test | | Casting Crack | Maximum Corrosion Depth (μm) | Corrosion Loss (mg/cm²) Erosion · corrosion test | | | | Machinability Cutting Main component (N) |
|---|---|---|---|---|---|---|---|---|---|---|
| | | Castability | Grain Size | | | I | II | III | IV | |
| EMBODIMENT 1 | 100 | Δ | ○ | Δ | | | | | | |
| 2 | 200 | Δ | Δ | | | | | | | |
| 3 | 45 | ○ | ○ | | | | | | | |
| 4 | 120 | Δ | Δ | Δ | | | | | | |
| 5 | 250 | Δ | Δ | | | | | | | |
| 6 | 90 | Δ | ○ | ○ | | 15 | | | 190 | |
| 7 | 250 | Δ | Δ | | | 23 | 37 | | | |
| 8 | 65 | ○ | ○ | | 50 | 25 | 46 | 138 | 305 | |
| 9 | 40 | ○ | ○ | ○ | 20 | | | | | |
| 10 | 35 | ○ | ○ | | 10 or less | 20 | 34 | 120 | 208 | |
| 11 | 40 | ○ | ○ | ○ | 10 or less | 19 | 33 | 120 | 233 | |
| 12 | 70 | ○ | ○ | ○ | 10 or less | | | | | |
| 13 | 100 | ○ | Δ | ○ | | 18 | 33 | 118 | 225 | |
| 14 | 150 | Δ | Δ | | | | | | | |
| 15 | 300 | Δ | Δ | Δ | 20 | 20 | 38 | 128 | 250 | 95 |
| 16 | 150 | Δ | Δ | Δ | 10 or less | 19 | 35 | 122 | 232 | 94 |
| 17 | 90 | ○ | Δ | | 10 or less | 18 | 33 | 120 | 230 | 93 |
| 18 | 35 | ○ | ○ | ○ | 10 or less | 17 | 32 | 118 | 220 | 93 |
| 19 | 55 | ○ | ○ | ○ | 10 or less | 18 | 33 | 122 | 223 | 93 |
| 20 | 100 | ○ | ○ | Δ | 10 or less | | | | | 94 |
| 21 | 50 | ○ | ○ | ○ | 10 or less | | | | | |
| 22 | 280 | Δ | Δ | Δ | 30 | | | | | 94 |
| 23 | 200 | Δ | Δ | Δ | 10 or less | | | | | 94 |
| 24 | 60 | ○ | ○ | | 10 or less | | | | | 93 |
| 25 | 40 | ○ | ○ | ○ | 10 or less | | | | | 93 |
| 26 | 60 | ○ | ○ | ○ | 10 or less | | | | | |

| Casting No. | Tensile Strength (N/mm²) | Proof Stress (N/mm²) | Elongation (%) | Fatigue Strength (N/mm²) | Wear Loss (mg) | Semi-solid Metal castability |
|---|---|---|---|---|---|---|
| EMBODIMENT 1 | | | | | | |
| 2 | | | | | | |
| 3 | | | | | 1.3 | ○ |
| 4 | | | | | 2.8 | |
| 5 | | | | | | |
| 6 | | | | | | |
| 7 | | | | | | |
| 8 | | | | | | |
| 9 | 273 | 125 | 27 | 130 | 11 | |
| 10 | | | | | | ○ |
| 11 | 274 | 125 | 28 | 129 | 10 | ○ |
| 12 | | | | | | |
| 13 | 258 | 98 | 26 | 104 | 10 | |
| 14 | | | | | | |
| 15 | 249 | 95 | 24 | 96 | 11 | |
| 16 | 257 | 99 | 26 | | | |
| 17 | 258 | 104 | 27 | | | |

TABLE 5-continued

| | | | | | | |
|---|---|---|---|---|---|---|
| 18 | 270 | 116 | 28 | 120 | 10 | ○ |
| 19 | 264 | 111 | 28 | | | ○ |
| 20 | 259 | 101 | 26 | 108 | 11 | Δ |
| 21 | 268 | 122 | 28 | 125 | 10 | |
| 22 | | | | | | |
| 23 | 252 | 94 | 24 | 97 | 11 | |
| 24 | | | | | | |
| 25 | | | | | | |
| 26 | | | | | | |

TABLE 6

| | Casting No. | Tatur | | | Maximum Corrosion Depth (μm) | Corrosion Loss (mg/cm$^2$) Erosion·corrosion test | | | | Machinability | |
|---|---|---|---|---|---|---|---|---|---|---|---|
| | | Mean Grain Size (μm) | Shrinkage Test Castability | Grain Size | Casting Crack | | I | II | III | IV | Cutting Main component (N) | Chip type |
| EMBODIMENT | 27 | 80 | ○ | ○ | ○ | 10 or less | | | | | | |
| | 28 | 90 | ○ | ○ | | 10 or less | | | | | 95 | |
| | 29 | 120 | ○ | Δ | Δ | 10 or less | | | | | | |
| | 30 | 280 | | x | | 10 or less | | | | | 96 | |
| | 31 | 200 | | Δ | | 30 | | | | | | |
| | 32 | 60 | Δ | ○ | ○ | | 14 | 32 | 110 | 180 | 119 | a |
| | 33 | 120 | ○ | Δ | | | | | | | | |
| | 34 | 60 | ○ | ○ | ○ | | 18 | 28 | 109 | 234 | 114 | |
| | 35 | 35 | ○ | ○ | ○ | 10 or less | | | | | 102 | |
| | 36 | 150 | Δ | Δ | Δ | 10 or less | | | | | | |
| | 37 | 80 | ○ | ○ | ○ | 10 or less | 19 | 37 | 125 | 232 | | |
| | 38 | 60 | ○ | ○ | ○ | 30 | 22 | 37 | | | | |
| | 39 | 90 | ○ | ○ | | 20 | 26 | 45 | | | | |
| | 40 | 60 | ○ | ○ | | 10 or less | 22 | 38 | 132 | 256 | | |
| | 41 | 80 | ○ | ○ | ○ | 10 or less | | | | | | |
| | 42 | 250 | Δ | Δ | Δ | | | | | | | |
| | 43 | 80 | Δ | ○ | | | | | | | | |
| | 44 | 40 | ○ | ○ | ○ | 10 or less | | | | | 145 | |
| | 45 | 40 | ○ | ○ | ○ | 10 or less | | | | | 194 | |
| | 46 | 50 | ○ | ○ | | 10 or less | | | | | 228 | |
| | 47 | 150 | Δ | Δ | Δ | 10 or less | | | | | 109 | |
| | 48 | 60 | ○ | ○ | ○ | 10 or less | | | | | 107 | a |
| | 49 | 70 | ○ | ○ | ○ | 10 or less | | | | | 107 | a |
| | 50 | 80 | ○ | ○ | ○ | 10 or less | | | | | 109 | a |
| | 51 | 40 | ○ | ○ | ○ | 10 or less | 19 | 34 | 124 | 228 | 110 | |
| | 52 | 60 | ○ | ○ | | 40 | | | | | 100 | |

| | Casting No. | Tensile Strength (N/mm$^2$) | Proof Stress (N/mm$^2$) | Elongation (%) | Fatigue Strength (N/mm$^2$) | Wear Loss (mg) | Semi-solid Metal castability |
|---|---|---|---|---|---|---|---|
| EMBODIMENT | 27 | 255 | 100 | 20 | | | |
| | 28 | | | | | | |
| | 29 | | | | | | |
| | 30 | 230 | 92 | 17 | | | |
| | 31 | 335 | 156 | 28 | 168 | 10 | |
| | 32 | | | | | | |
| | 33 | | | | | | |
| | 34 | | | | | | |
| | 35 | | | | | | |
| | 36 | | | | | | |
| | 37 | | | | | | |
| | 38 | | | | | | |
| | 39 | | | | | | |
| | 40 | | | | | | |
| | 41 | | | | | | |
| | 42 | | | | | | |
| | 43 | | | | | 1.1 | |
| | 44 | | | | | | |
| | 45 | | | | | | |
| | 46 | | | | | | |
| | 47 | 220 | 92 | 14 | 95 | | Δ |

TABLE 6-continued

| | | | | | | |
|---|---|---|---|---|---|---|
| 48 | 254 | 112 | 21 | 118 | 29 | ○ |
| 49 | 252 | 110 | 22 | 114 | 29 | ○ |
| 50 | 235 | 105 | 16 | | | ○ |
| 51 | 265 | | 22 | 132 | | |
| 52 | | | | | | |

TABLE 7

| | Casting No. | Mean Grain Size (μm) | Tatur Shrinkage Test Castability | Tatur Shrinkage Test Grain Size | Tatur Shrinkage Test Casting Crack | Maximum Corrosion Depth (μm) | Corrosion Loss (mg/cm²) Erosion·corrosion test I | II | III | IV | Machinability Cutting Main component (N) | Tensile Strength (N/mm²) | Proof Stress (N/mm²) | Elongation (%) | Fatigue Strength (N/mm²) | Wear Loss (mg) |
|---|---|---|---|---|---|---|---|---|---|---|---|---|---|---|---|---|
| EMBODIMENT | 53 | 90 | ○ | ○ | ○ | 10 or less | | | | | 114 | 255 | 108 | 24 | 115 | |
| | 54 | 80 | ○ | ○ | | | | | | | 105 | 245 | 107 | 21 | 105 | |
| | 55 | 80 | ○ | ○ | ○ | | | | | | | | | | | |
| | 56 | 35 | ○ | ○ | ○ | 10 or less | 18 | 33 | 118 | 235 | 102 | 260 | 121 | 18 | 132 | |
| | 57 | 80 | △ | △ | △ | | 15 | 34 | 112 | 196 | | | | | | 3.7 |
| | 58 | 40 | ○ | ○ | ○ | 10 or less | | | | | | | | | | |
| | 59 | 45 | ○ | ○ | ○ | 10 or less | 18 | 34 | 115 | 242 | 145 | 272 | 118 | 26 | 125 | |
| | 60 | 35 | ○ | ○ | ○ | 10 or less | | | | | 107 | 263 | 115 | 22 | | |
| | 61 | 40 | ○ | ○ | | 10 or less | | | | | | | | | | |
| | 62 | 35 | ○ | ○ | | 10 or less | | | | | | | | | | |
| | 63 | 90 | △ | △ | | 10 or less | | | | | | | | | | |
| | 64 | 80 | ○ | ○ | | 10 or less | | | | | 95 | 258 | 100 | 25 | | |
| | 65 | 40 | ○ | ○ | ○ | 10 or less | | | | | 93 | 276 | 125 | 25 | 133 | |
| | 66 | 35 | ○ | ○ | ○ | 10 or less | | | | | | | | | | |
| | 67 | 120 | △ | △ | △ | | | | | | 94 | 258 | 101 | 26 | | |
| | 68 | 50 | ○ | ○ | ○ | 10 or less | 18 | 33 | 117 | 232 | | | | | | |
| | 69 | 40 | ○ | ○ | | 20 | | | | | | | | | | |
| | 70 | 100 | ○ | △ | | | | | | | | | | | | |
| | 71 | 35 | ○ | ○ | ○ | 10 or less | | | | | | | | | | |
| | 72 | 60 | ○ | ○ | ○ | 10 or less | | | | | 108 | 254 | 113 | 21 | | |
| | 73 | 45 | ○ | ○ | | | | | | | | | | | | |
| | 74 | 40 | ○ | ○ | | 10 or less | | | | | | | | | | |
| | 75 | 60 | ○ | ○ | ○ | 10 or less | | | | | | | | | | |

TABLE 8

| Casting No. | | Tatur Mean Grain Size (μm) | Shrinkage Test Castability | Shrinkage Test Grain Size | Casting Crack | Maximum Corrosion Depth (μm) | Corrosion Loss (mg/cm²) Erosion·corrosion test I | II | III | IV | Machinability Cutting Main component (N) | Chip type |
|---|---|---|---|---|---|---|---|---|---|---|---|---|
| COMPARATIVE EXAMPLE | 101 | 450 | Δ | x | | | | | | | | |
| | 102 | 700 | x | x | x | 50 | 23 | 44 | 134 | 265 | 96 | |
| | 103 | 320 | x | x | | 20 | 20 | 34 | 134 | 250 | 97 | |
| | 104 | 800 | x | x | x | 70 | | | | | 96 | |
| | 105 | 320 | x | Δ | x | 10 or less | | | | | 97 | |
| | 106 | 1000 | x | x | x | | 16 | 36 | 115 | 225 | 126 | e |
| | 107 | 800 | x | x | | | | | | | | |
| | 108 | 1200 | x | x | x | 10 or less | | | | | 112 | e |
| | 109 | 1000 | x | x | x | | 16 | 38 | 128 | 235 | | |
| | 110 | 550 | x | x | x | 10 or less | 20 | 35 | 124 | 263 | 97 | |
| | 111 | 500 | x | x | x | 10 or less | | | | | | |
| | 112 | 550 | x | x | x | 10 or less | | | | | | |
| | 113 | | x | x | x | 10 or less | 19 | 35 | 122 | 258 | 96 | |
| | 114 | | x | x | x | 10 or less | 20 | 38 | 129 | 265 | 104 | |
| | 115 | | x | x | x | | 20 | 36 | 128 | 261 | 107 | |
| | 116 | | x | x | x | 800 | 64 | 118 | 423 | 840 | 91 | |
| | 117 | 500 | x | x | x | 50 | | | | | | |

| Casting No. | | Tensile Strength (N/mm²) | Proof Stress (N/mm²) | Elongation (%) | Fatigue Strength (N/mm²) | Wear loss (mg) | Cold workability | Semi-solid Metal castability |
|---|---|---|---|---|---|---|---|---|
| COMPARATIVE EXAMPLE | 101 | | | | | | | |
| | 102 | 218 | 82 | 19 | 85 | 12 | | x |
| | 103 | 250 | 96 | 20 | 98 | 13 | | |
| | 104 | 235 | 80 | 22 | 83 | 12 | | |
| | 105 | 225 | 95 | 14 | | | | |
| | 106 | 269 | 94 | 15 | 98 | 13 | | x |
| | 107 | | | | | 4.5 | | |
| | 108 | 199 | 80 | 6 | 83 | 38 | x | x |
| | 109 | | | | | 7.5 | | |
| | 110 | 235 | 84 | 19 | | | | |
| | 111 | | | | | | | |
| | 112 | | | | | | | |
| | 113 | 234 | 82 | 23 | 85 | 12 | | |
| | 114 | 198 | 81 | 8 | 78 | 30 | | |
| | 115 | 214 | 80 | 12 | 82 | | | |
| | 116 | 282 | 83 | 15 | 86 | 250 | | |
| | 117 | 242 | 85 | 19 | 84 | | | x |

The invention claimed is:

1. A copper alloy casting comprising a copper alloy comprising:
   Sn: 0.5 to 15 mass %;
   Zr: 0.001 to 0.049 mass %;
   P: 0.01 to 0.35 mass %;
   one or more elements selected from
      Pb: 0.01 to 15 mass %,
      Bi: 0.01 to 15 mass %,
      Se: 0.01 to 1.2 mass %, and
      Te: 0.05 to 1.2 mass %;
   Zn: 0.27 to 12.59 mass %; and
   Cu: 73 mass % or more serving as a remainder,
   wherein the copper alloy of the copper alloy casting satisfies the following conditions,
      f1=[P]/[Zr]=0.5 to 100,
      f2=([Zn]+3[Sn])/[Zr]=300 to 15000,
      f3=([Zn]+3[Sn])/[P]=40 to 2500, and
      f4=[Zn]+3[Sn]=10 to 43, and
   the content of each element 'a' is expressed as mass %
   wherein the total content of α, γ and δ-phases of the copper alloy in the copper alloy casting in a solid metal state is 95% or more,
   wherein the copper alloy has grains with a mean grain size of 300 μm or less of the copper alloy casting.

2. The copper alloy casting according to claim 1, wherein the copper alloy of the copper alloy casting further comprises:
   one or more elements selected from Al: 0.005 to 0.5 mass %, Mn: 0.01 to 0.5 mass %, and Mg: 0.001 to 0.2 mass %.

3. The copper alloy casting according to claim 1, wherein the copper alloy of the copper alloy casting further comprises:
   As: 0.02 to 0.2 mass % and/or Sb: 0.02 to 0.2 mass %.

4. The copper alloy casting according to claim 1, wherein the copper alloy of the copper alloy casting further comprises:
   one or more elements selected from Al: 0.005 to 0.5 mass %, Mn: 0.01 to 0.5 mass %, and Mg: 0.001 to 0.2 mass %;
   and one or more elements selected from As: 0.02 to 0.2 mass % and Sb: 0.02 to 0.2 mass %.

5. The copper alloy casting according to any one of claims 2-4, wherein the copper alloy casting is a water contact metal fitting used continuously or temporarily in contact with water, or a structural material thereof.

6. The copper alloy casting according to any one of claims 2-4, wherein the copper alloy casting is a water contact metal fitting continuously or temporarily in contact with a friction engaging member.

7. The copper alloy casting according to any one of claims 1 to 6, wherein the copper alloy of the copper alloy casting satisfies the following condition, f5=[Cu]−0.5[Sn]−3[P]+0.5([Pb]+[Bi]+[Se]+[Te])−0.5([As]+[Sb])−1.8[Al]+[Mn]+[Mg]=60 to 90, and the content of each element 'a' is expressed as [a] mass %, and an element 'a' that is not contained in the copper alloy casting is expressed as [a]=0.

8. The copper alloy casting according to claim 7, wherein a peritectic reaction occurs during melt-solidification of the copper alloy of the copper alloy casting.

9. The copper alloy casting according to claim 7, wherein when the copper alloy is in a semi-solid metal state, a two-dimensional shape of the grains of the copper alloy during melt-solidification is circular, substantially circular, oval, cross-like, acicular, or polygonal.

10. The copper alloy casting according to claim 7, wherein the α-phase is divided finely in the matrix, and γ-phase, δ-phase or high Sn-concentrated area that is generated by segregation is distributed uniformly in the matrix of the copper alloy in the copper alloy casting in a solid metal state.

11. The copper alloy casting according to claim 7, wherein the copper alloy casting is a water contact metal fitting used continuously or temporarily in contact with water, or a structural material thereof.

12. The copper alloy casting according to any one of claims 1 to 6, wherein the copper alloy of the copper alloy casting comprises Fe or Ni, or Fe and Ni, as inevitable impurities, wherein, when either Fe or Ni is contained, the content thereof is restricted to be 0.3 mass % or less, and when both Fe and Ni are contained, a total content of Fe and Ni is restricted to be 0.35 mass % or less.

13. The copper alloy casting according to claim 12, wherein when the copper alloy is in a semi-solid metal state, a two-dimensional shape of the grains of the copper alloy during melt-solidification is circular, substantially circular, oval, cross-like, acicular, or polygonal.

14. The copper alloy casting according to claim 12, wherein the copper alloy casting is a water contact metal fitting used continuously or temporarily in contact with water, or a structural material thereof.

15. The copper alloy casting according to claim 12, wherein the copper alloy casting is a water contact metal fitting continuously or temporarily in contact with a friction engaging member.

16. The copper alloy casting according to any one of claims 1 to 6, wherein a primary crystal is α-phase during melt-solidification of the copper alloy of the copper alloy casting.

17. The copper alloy casting according to claim 10, wherein the copper alloy casting is a water contact metal fitting used continuously or temporarily in contact with water, or a structural material thereof.

18. The copper alloy casting according to claim 1, wherein the copper alloy of the final copper alloy casting in the solid metal state is a solidified form of the copper alloy melted in air.

* * * * *